US012147603B2

(12) United States Patent
Furman et al.

(10) Patent No.: US 12,147,603 B2
(45) Date of Patent: Nov. 19, 2024

(54) INTERACTIVE ELECTRONIC CONTENT DELIVERY IN COORDINATION WITH RAPID DECODING OF BRAIN ACTIVITY

(71) Applicant: ARCTOP LTD, Tel Aviv-Jaffa (IL)

(72) Inventors: Daniel Furman, San Francisco, CA (US); Eitan Kwalwasser, Tel Aviv (IL)

(73) Assignee: Arctop LTD, Tel Aviv-Jaffa (IL)

( * ) Notice: Subject to any disclaimer, the term of this patent is extended or adjusted under 35 U.S.C. 154(b) by 0 days.

(21) Appl. No.: 18/303,382

(22) Filed: Apr. 19, 2023

(65) Prior Publication Data

US 2023/0259208 A1 Aug. 17, 2023

Related U.S. Application Data

(63) Continuation of application No. 16/762,262, filed as application No. PCT/US2018/061958 on Nov. 20, 2018, now Pat. No. 11,662,816.
(Continued)

(51) Int. Cl.
*G06F 3/01* (2006.01)
*A61B 5/00* (2006.01)
(Continued)

(52) U.S. Cl.
CPC ............ *G06F 3/015* (2013.01); *A61B 5/372* (2021.01); *G06F 1/163* (2013.01); *G06F 21/31* (2013.01);
(Continued)

(58) Field of Classification Search
CPC ... G06F 3/01; G06F 3/03; G06F 3/015; G06F 3/0484; G06F 21/31; G06F 21/32;
(Continued)

(56) References Cited

U.S. PATENT DOCUMENTS 9,983,670 B2 5/2018 Coleman et al.
2007/0173733 A1 7/2007 Le et al.
(Continued)

FOREIGN PATENT DOCUMENTS

WO    WO 2016/118811 A3    7/2016

OTHER PUBLICATIONS

PCT International Search Report and Written Opinion, International Application No. PCT/US2018/061958, Feb. 11, 2019, 14 Pages.
(Continued)

*Primary Examiner* — Chanh D Nguyen
*Assistant Examiner* — Nguyen H Truong
(74) *Attorney, Agent, or Firm* — Fenwick & West LLP

(57) ABSTRACT

A method and system for providing a user with virtual objects within an environment, characterizing interactions with the virtual objects using a brain computer interface, and modulating features of the virtual objects based upon improved classifiers associated with the interactions. The method and system can be used to rapidly customize virtual objects to a specific user in applications related to increasing engagement with traditional and new media content, virtual and augmented reality products, streamlining interactions with input devices in digital and physical environments, providing user authentication tools, providing more secure cybersecurity features, and delivering tailored content to users.

20 Claims, 14 Drawing Sheets

Related U.S. Application Data

(60) Provisional application No. 62/589,421, filed on Nov. 21, 2017.

(51) Int. Cl.
 *A61B 5/372* (2021.01)
 *G06F 1/16* (2006.01)
 *G06F 21/31* (2013.01)
 *G06N 20/00* (2019.01)
 *G06T 19/20* (2011.01)
 *G16H 40/60* (2018.01)

(52) U.S. Cl.
 CPC ............ *G06N 20/00* (2019.01); *G06T 19/20* (2013.01); *G16H 40/60* (2018.01); *G06F 2221/2103* (2013.01); *G06F 2221/2139* (2013.01); *G06T 2219/2021* (2013.01)

(58) Field of Classification Search
 CPC .... G06F 21/36; G06F 21/40; G06F 2203/011; G06F 17/10; G06F 17/20; G06F 2221/2103; G06F 2221/2139; G06F 1/163; G06T 11/60; G06T 19/00; G06T 19/20; G06T 2219/2021; G10H 2220/376; A61B 5/00; A61B 5/08; A61B 5/091; A61B 5/01; A61B 5/16; A61B 5/087; A61B 5/0476; A61B 5/0205; A61B 5/04; A61B 5/048; A61B 5/0482; A61B 5/0478; A61B 5/117; A61B 5/0484; A61B 5/291; A61B 5/31; A61B 5/0006; A61B 5/396; A61B 5/37; H04N 21/42201; G05B 2219/39292; G05B 2219/39385; A61N 1/05; A61N 1/36; G16H 40/60; G06N 20/00

See application file for complete search history.

(56) References Cited

U.S. PATENT DOCUMENTS

| | | |
|---|---|---|
| 2010/0137734 A1 | 6/2010 | Digiovanna et al. |
| 2011/0035689 A1 | 2/2011 | Snyder |
| 2011/0144452 A1 | 6/2011 | Shin et al. |
| 2014/0112556 A1 | 4/2014 | Kalinli-Akbacak |
| 2014/0171757 A1* | 6/2014 | Kawato ................. A61B 5/316 600/545 |
| 2015/0066104 A1 | 3/2015 | Wingeier et al. |
| 2016/0103487 A1 | 4/2016 | Crawford et al. |
| 2017/0043167 A1 | 2/2017 | Widge et al. |
| 2017/0251945 A1* | 9/2017 | Nick ...................... A61B 5/743 |
| 2018/0188807 A1 | 7/2018 | Cimenser et al. |
| 2019/0073030 A1* | 3/2019 | Lee ........................ B25J 13/087 |
| 2019/0101985 A1 | 4/2019 | Sajda et al. |

OTHER PUBLICATIONS

He, B. et al. "Brain-Computer Interfaces," *Neural Engineering*, 2013, pp. 87-152.

United States Office Action, U.S. Appl. No. 16/762,262, Sep. 13, 2022, 15 pages.

United States Office Action, U.S. Appl. No. 16/762,262, Mar. 17, 2022, 14 pages.

* cited by examiner

Different time scales associated with feature modulation for each feature and/or different features Body Transformation/Complex Examples Different time scales associated with feature modulation for each feature and/or different features

PROBE EXAMPLES

Animations and/or Audio

INTERACTIVE ELECTRONIC CONTENT DELIVERY IN COORDINATION WITH RAPID DECODING OF BRAIN ACTIVITY

CROSS REFERENCE TO RELATED APPLICATIONS

This application is a continuation of U.S. patent application Ser. No. 16/762,262 filed 7 May 2020, which is a National Stage of International Application No. PCT/US2018/061958 filed 20 Nov. 2018, which claims the benefit of U.S. Provisional Application No. 62/589,421 filed 21 Nov. 2017, the disclosures of which are incorporated in their entirety herein by this reference.

BACKGROUND

The present disclosure generally relates to neural signal processing, and specifically to a system and method for interactive content delivery coordinated with rapid decoding of brain activity, using a brain-computer interface.

Brain-computer interface (BCI) systems and methods can be used to interface users seamlessly with their environment and to enhance user experiences in digital worlds. Such BCI systems can be used to connect one or more users to the electronic universe to provide a mechanism for security (e.g., authentication, authorization) in relation to access of sensitive information and delivery of content customized to users, and/or for any other suitable purpose. In relation to delivery of customized content, current systems are unable to rapidly decode neurological activity of a user and to coordinate decoding with provision of digital content tailored to users. Current systems further have deficiencies in their abilities to use digital content for authentication of user identities, based on signals capturing neurological responses to the digital content.

SUMMARY

Electronic content provided to a user can be used to enhance interactions between users and environments (e.g., physical environments, virtual environments, etc.), and to help a user feel more connected to an environment in a secure manner. The method(s) and system(s) described herein reinforce relationships between users and digital objects, include architecture for improving decoding of neurological activity of users in relation to content provided in a virtual environment, where the content has dynamically modifiable features, and includes functionality for authenticating and providing tailored content to users.

One or more embodiments of the system(s) described include hardware systems coupled to a BCI device worn at a head region of a user, where the BCI includes sensors that receive neurological signals from the brain of the user. The hardware systems include electronics for receiving and conditioning outputs of the BCI and transmitting digital content to the user at a display, and computing architecture developed to generate classifications of neurological activity of the user as the user interacts with the digital content, modulate features of the digital content based on the classified neurological activity, and contemporaneously modulate parameters of brain decoding portions of the computing architecture as the user interacts with the modulated digital content. The computing architecture also processes input neurological signals to determine user identities and cognitive states (e.g., states of stress, affective states, etc.) based on responses to digital content, and generates content tailored to the user based on the user's identity and state. Such tailored content can include entertainment experiences, information of interest to the user, rewards, augmented and virtual reality experiences and/or other tailored content. Such tailored aspects of the environment can also be used to maintain a state of comfort or "homeostasis" between a user and a virtual environment that the user is interacting with.

The system(s) and method(s) described herein can be adapted to be used by a user who is remote from a research or clinical environment, where the user is moving about in his or her daily life. The method(s) and/or system(s) can thus be provided to enhance user experiences with content provided in an augmented reality setting and/or virtual reality setting.

The figures depict various embodiments for purposes of illustration only. One skilled in the art will readily recognize from the following discussion that alternative embodiments of the structures and methods illustrated herein may be employed without departing from the principles described herein.

DETAILED DESCRIPTION

1. System Environment

Figure 1A:
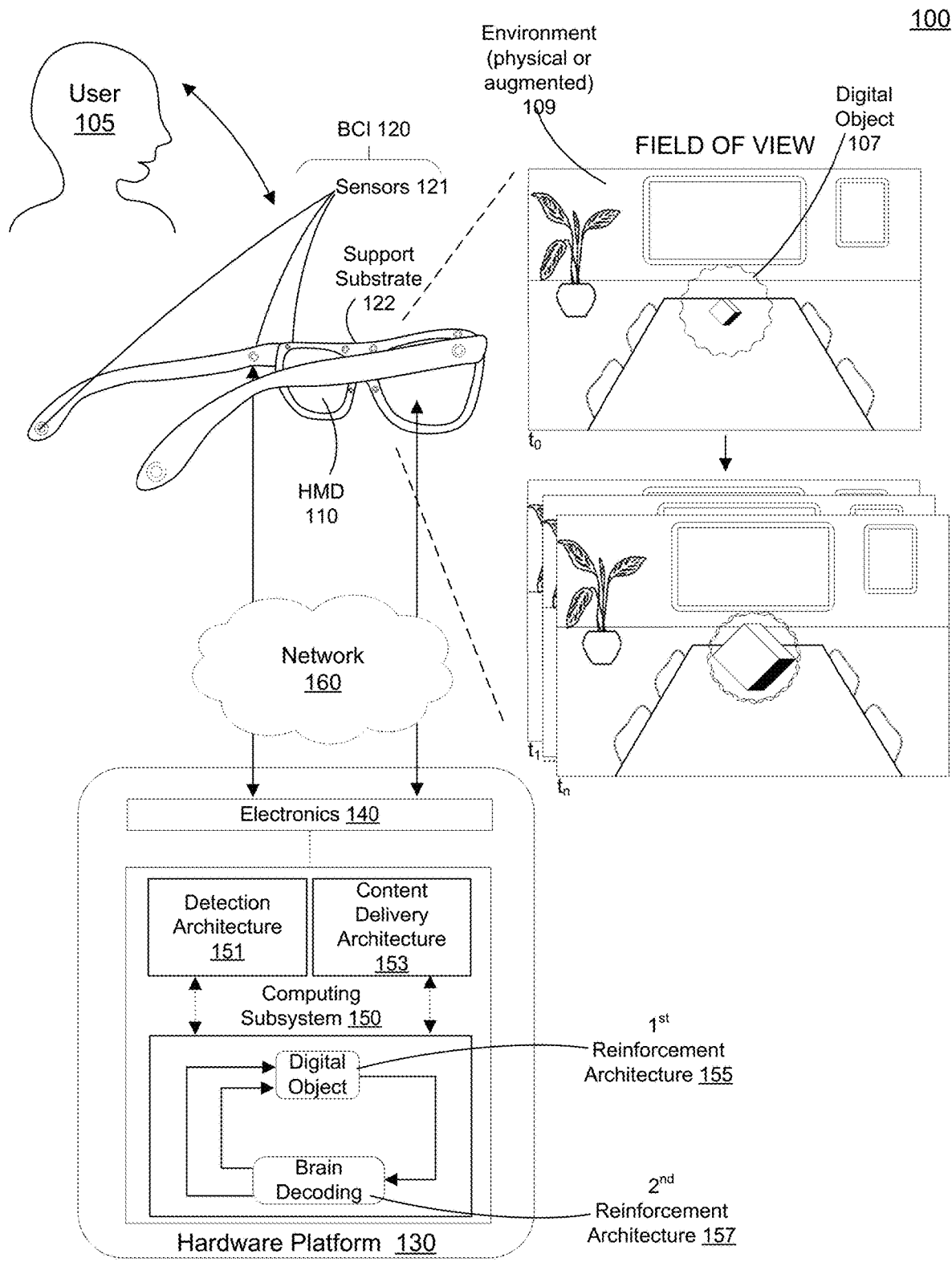
FIG. 1A depicts a schematic of a system environment for interactive electronic content delivery in coordination with rapid decoding of brain activity, in accordance with one or more embodiments.
Figure 1B:
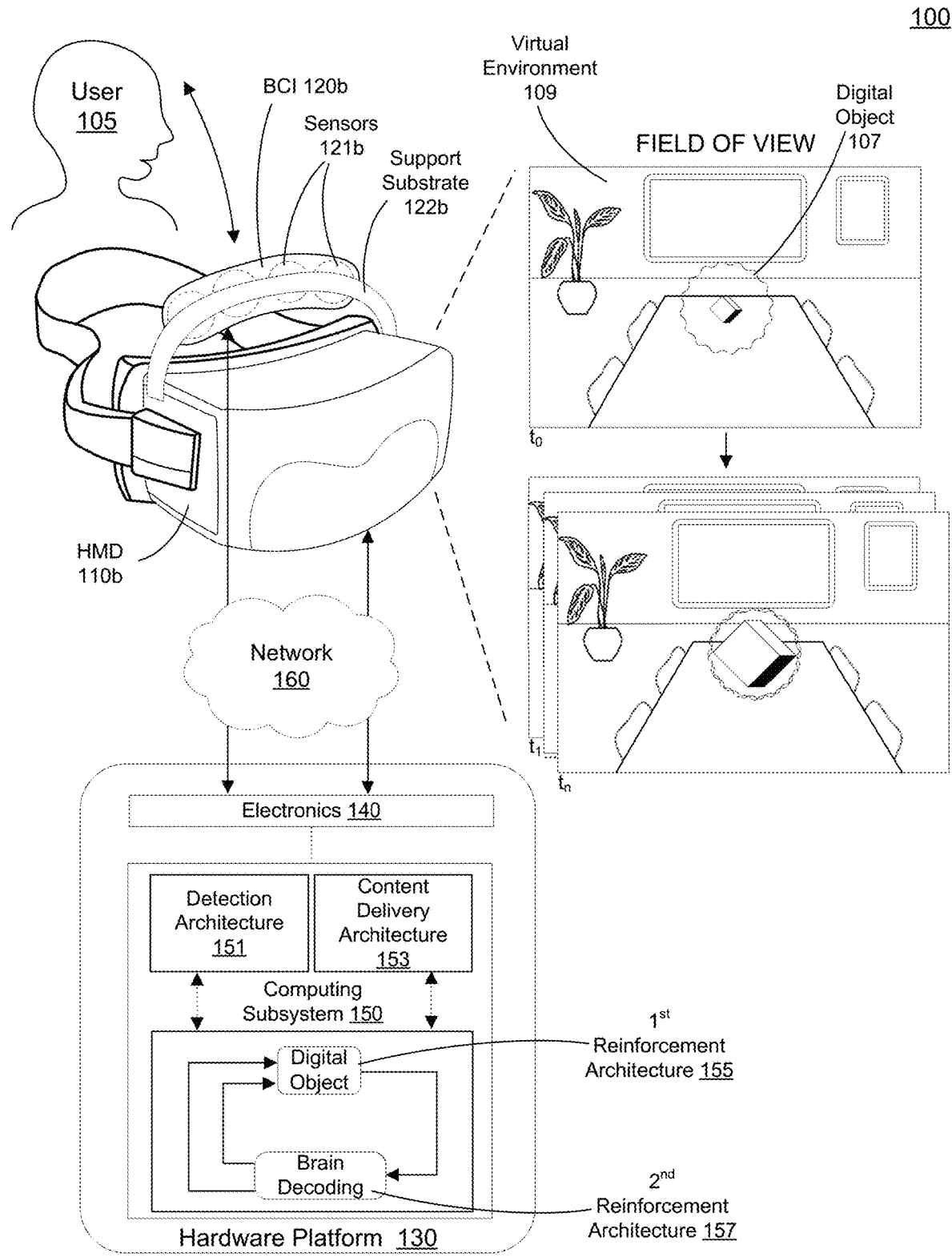
FIG. 1B depicts a schematic of an alternative embodiment of the system environment shown in FIG. 1A.

FIG. 1A depicts a system environment of a system 100 for interactive electronic content delivery in coordination with rapid decoding of brain activity, in accordance with one or more embodiments. FIG. 1B depicts an alternative embodiment of the system environment shown in FIG. 1A. The system 100 shown in FIG. 1 includes a head-mounted display (HMD) 110 coupled with a brain-computer interface (BCI) 120 including an array of sensors for detecting a neural signal stream from a user 105 as the user interacts with content provided through the HMD. The system 100 also includes a hardware platform 130 configured to couple with the HMD 110 and the BCI 120, where the hardware platform 130 includes an electronics subsystem 140 for receiving and conditioning outputs of the BCI 120, as well as reinforcement architecture for rapidly decoding brain activity of the user and adjusting features of a virtual environment in response to brain activity decoding processes.

The embodiments of the system 100 function to reinforce relationships between users and digital objects/environments, include architecture for improving decoding of neurological activity of users in relation to content provided in a virtual environment, where the content has dynamically modifiable features, and include functionality for authenticating and providing tailored content to users. Such tailored aspects of the virtual environment and objects can also be used to maintain a state of comfort or "homeostasis" between a user and a virtual environment that the user is interacting with.

1.1 System—HMD and BCI

The HMD 110 is configured to be worn by a user and to deliver digital content generated by the architecture of the hardware platform 130 to the user. The HMD 110 includes a display for rendering electronic content to a user. As described in relation to the methods below, content rendered by the display of the HMD 110 can include digital objects 107 and/or virtual environments 109 within a field of view associated with the display. The digital objects 107 and/or virtual environments 109 have modulatable features that can be used to prompt interactions with a user, as described below. The HMD 110 can additionally include one or more of: power management-associated devices (e.g., charging units, batteries, wired power interfaces, wireless power interfaces, etc.), fasteners that fasten wearable components to a user in a robust manner that allows the user to move about in his/her daily life, and any other suitable components. The HMD 110 can also include interfaces with other computing devices, such as a mobile computing device (e.g., tablet, smartphone, smartwatch, etc.) that can receive inputs that contribute to control of content delivered through the HMD 110, and/or deliver outputs associated with use of the HMD 110 by the user.

The BCI 120 includes a set of sensors 121 configured to detect neurological activity from the brain of the user, during use. In one embodiment, the set of sensors 121 include electrodes for electrical surface signal (e.g., electroencephalogram (EEG) signal, electrocorticography (ECoG) signal, etc.) generation, where the set of sensors 121 can include one or more of electrolyte-treated porous materials, polymer materials, fabric materials, or other materials that can form an electrical interface with a head region of a user. In alternative embodiments, the set of sensors 121 can include sensors operable for one or more of: magnetoencephalography (MEG), positron emission tomography (PET), functional magnetic resonance imaging (fMRI), single neuron signal sensing (e.g., using neurotrophic electrodes, using multi-unit arrays), and other neurosensing modalities. In still alternative embodiments, the set of sensors 121 can include sensors operable for optical neurosensing modalities including one or more of: diffuse optical tomography (DOT), near-infrared spectroscopy (fNIRS), functional time-domain near-infrared spectroscopy (TD-fNIRS), diffuse correlation spectroscopy (DCS), speckle contrast optical tomography (SCOT), time-domain interferometric near-infrared spectroscopy (TD-iNIRS), hyperspectral imaging, polarization-sensitive speckle tomography (PSST), spectral decorrelation, and other imaging modalities.

As shown in FIGS. 1A and 1B, the BCI 120 can be coupled to one or more portions of the HMD 110, such that the user wears a single apparatus having both content provision functions and neurological signal detection and transmission functions.

As shown in FIG. 1A, the sensors 121 of the BCI 120 can be coupled to a support substrate 122, where the support substrate 122 can include portions configured to arch over a frontal and/or pre-frontal portion of the head of the user during use, as well as temporal portions, parietal portions, and maxillofacial regions of the user's head. In embodiments, the support substrate 122 can form one or more of: frames, temple pieces, and nose bridge of eyewear of the HMD 110, such that the user is provided with display and sensing functionality in a compact form factor. As shown in FIG. 1A, the sensors 121 of the BCI 120 are coupled inward facing portions of the temple pieces, frame, and nose bridge of the support substrate 122 to interface with appropriate portions of the user's head and/or face during use. As such, the HMD 110 and the BCI 120 can share computing components, power management components, and/or other electronics in a configuration as a single apparatus.

As shown in the alternative embodiment of FIG. 1B, the sensors 121b of the BCI 120b can be coupled to a support substrate 122b configured to arch over a frontal and/or pre-frontal portion of the head of the user during use, where the sensors 121b of the BCI 120b are coupled to a posterior portion of the support substrate 122b to contact the head of the user during use. As shown in FIG. 1B, terminal regions of the support substrate 122b are coupled to (e.g., electromechanically coupled to, electrically coupled to, mechanically coupled to) to bilateral portions of housing portions of the HMD 110b. As such, the HMD 110b and the BCI 120b can share computing components, power management components, and/or other electronics.

However, in still alternative embodiments, the components of the BCI 120, 120b can be coupled to the HMD 110, 110b in another manner. In still alternative embodiments, the BCI 120, 120b can be physically distinct from the HMD 110, 110b, such that the BCI 120, 120b and the HMD 110, 110b are not configured as a single apparatus.

1.2 System—Hardware Platform

The hardware platform 130 also includes a computing subsystem 150 in communication with the electronics subsystem 140, where the computing subsystem can include a non-transitory computer-readable storage medium containing computer program code for operating in different modes associated with digital object and/or virtual environment modulation, and neural activity decoding for reinforcement of user relationships with provided content. The computing subsystem 150 can thus include content delivery architecture 153 that allows the system 100 to operate in a content delivery mode that provides a digital object to a user within a virtual environment through the HMD.

The computing subsystem can also include detection architecture 151 that allows the system 100 to operate in a detection mode that detects a neural signal stream from the BCI, as the user interacts with the digital object. The detection architecture 151 includes structures with operation modes for determining activity (e.g., in relation to spectral content, in relation to neural oscillations, in relation to evoked potentials, in relation to event-related potentials, in relation to different frequency bands of activity, in relation to combinations of activity, etc.), from different electrode channels associated with different brain regions of the user, in order to determine activity states in different regions associated with different brain states. In embodiments, the different brain states analyzed can include one or more of: an alertness state (e.g., a sleep state, alertness level), a state of focus (e.g., focused, distracted, etc.), an emotional state (e.g., happy, angry, sad, bored, scared, calm, confused, surprised, etc.), a mental health state (e.g., a state of anxiety, a state of depression, a state characterized in a manual of mental health conditions, etc.), a neurological health state (e.g. seizure, migraine, stroke, dementia, etc.), a state of sobriety, a state of overt/covert attention, a state of reaction to sensory stimuli, a state of spatial orientation, a state of cognitive load (e.g. of being overloaded), a state of flow, a state of entrancement, a state of imagery (e.g. of motor action, of visual scenes, of sounds, of procedures, etc.), a memory function state (e.g. encoding effectively, forgetting, etc), and/or any other suitable brain activity state.

In relation to reinforcement of relationships between the user and digital content and reinforcement of performance of brain activity decoding processes in a coordinated manner, the computing subsystem 150 also includes a first reinforcement architecture 155 that generates a classification of a neurological activity of the user upon processing neural signals from the BCI with a decoding algorithm, and reinforces a relationship between the user and the digital object upon modulating a set of modulation features of the digital object based on the outputs of the decoding algorithm. The computing subsystem 150 also includes a second reinforcement architecture 157 that modulates a set of parameters of the decoding algorithm based upon interactions between the user and the digital object. The first and the second reinforcement architectures 155, 157 can define loops that operate contemporaneously with each other as neural signals from the user are acquired in the detection mode, where convergence of the mutual learning framework results in rapid decoding of brain activity for each user. In alternative configurations, different and/or additional components may be included in the system 100 to promote or otherwise enhance user engagement with digital content, to provide security features, and/or to promote rapid decoding of neurological activity of the user.

The computing subsystem 150 can thus include computing subsystems implemented in hardware modules and/or software modules associated with one or more of: personal computing devices, remote servers, portable computing devices, cloud-based computing systems, and/or any other suitable computing systems. Such computing subsystems can cooperate and execute or generate computer program products comprising non-transitory computer-readable storage mediums containing computer code for executing embodiments, variations, and examples of the methods described below. As such, portions of the computing subsystem 150 can include architecture for implementing embodiments, variations, and examples of the methods described below, where the architecture contains computer program stored in a non-transitory medium.

1.3 System—Communications

As shown in FIG. 1, the components of the system 100 can be configured to communicate with the through network 160, which can include any combination of local area and/or wide area networks, using both wired and/or wireless communication systems. In one embodiment, the computing subsystem 150 and/or other devices of the system (e.g., HMD 110, BCI 120) use standard communications technologies and/or protocols. For example, the network 160 includes communication links using technologies such as Ethernet, IEEE 802.11, worldwide interoperability for microwave access (WiMAX), 3G, 4G, 5G, code division multiple access (CDMA), global system for mobile communications (GSM), digital subscriber line (DSL), etc. Examples of networking protocols used for systems communication include transmission control protocol/Internet protocol (TCP/IP), hypertext transport protocol (HTTP), WebSocket (WS), and file transfer protocol (FTP). In some embodiments, all or some of the communication links of components of the system 100 may be encrypted using the secure extension of said protocol such as hypertext transfer protocol over secure sockets layer (SSL), WebSocket secure (WSS), secure file transfer program (SFTP) or any other suitable technique or techniques.

1.4 System—Other Sensors and Hardware

Devices of the system 100 can include additional sensor components for detecting aspects of user states, detecting contextual information (e.g., from a real-world environment of the user), and/or detecting aspects of interactions with electronic content generated by the computing subsystem 150 and transmitted through the HMD 110. Subsystems and/or sensors of can be coupled to, integrated with, or otherwise associated with the HMD 110 and/or BCI 120 worn by the user during interaction with provided content. Subsystems and/or sensors can additionally or alternatively be coupled to, integrated with, or otherwise associated with devices distinct from the HMD 110 and/or BCI 120 and communicate with the computing subsystem 150 during interactions between the user and provided electronic content.

Additional sensors can include audio sensors (e.g., directional microphones, omnidirectional microphones, etc.) to process captured audio associated with a user's interactions with the electronic content and/or environments surrounding the user. Sensors can additionally or alternatively include optical sensors (e.g., integrated with cameras) to process captured optically-derived information (associated any portion of an electromagnetic spectrum) associated with a user's interactions with the electronic content and/or environments surrounding the user. Sensors can additionally or alternatively include motion sensors (e.g., inertial measurement units, accelerometers, gyroscopes, etc.) to process captured motion data associated with a user's interactions with the electronic content and/or environments surrounding the user. Sensors can additionally or alternatively include biometric monitoring sensors including one or more of: skin conductance/galvanic skin response (GSR) sensors, sensors for detecting cardiovascular parameters (e.g., radar-based sensors, photoplethysmography sensors, electrocardiogram sensors, sphygmomanometers, etc.), sensors for detecting respiratory parameters (e.g., plethysmography sensors, audio sensors, etc.), body temperature sensors, and/or any other suitable biometric sensors. As such, additional sensor signals can be used by the hardware platform 130 for extraction of non-brain activity states (e.g., auxiliary biometric signals, auxiliary data, contextual data, etc.) that are relevant to determining user states. For instance, environmental factors (e.g., an analysis of environmental threats) and/or devices states (e.g., a user's device is wirelessly connected or connected otherwise to a network) can be used as inputs. The system 100 can thus process outputs of the sensors to extract features useful for guiding content modulation in near-real time according to the method(s) described below.

While the system(s) described above preferably implement embodiments, variations, and/or examples of the method(s) described below, the system(s) can additionally or alternatively implement any other suitable method(s).

Figure 2:
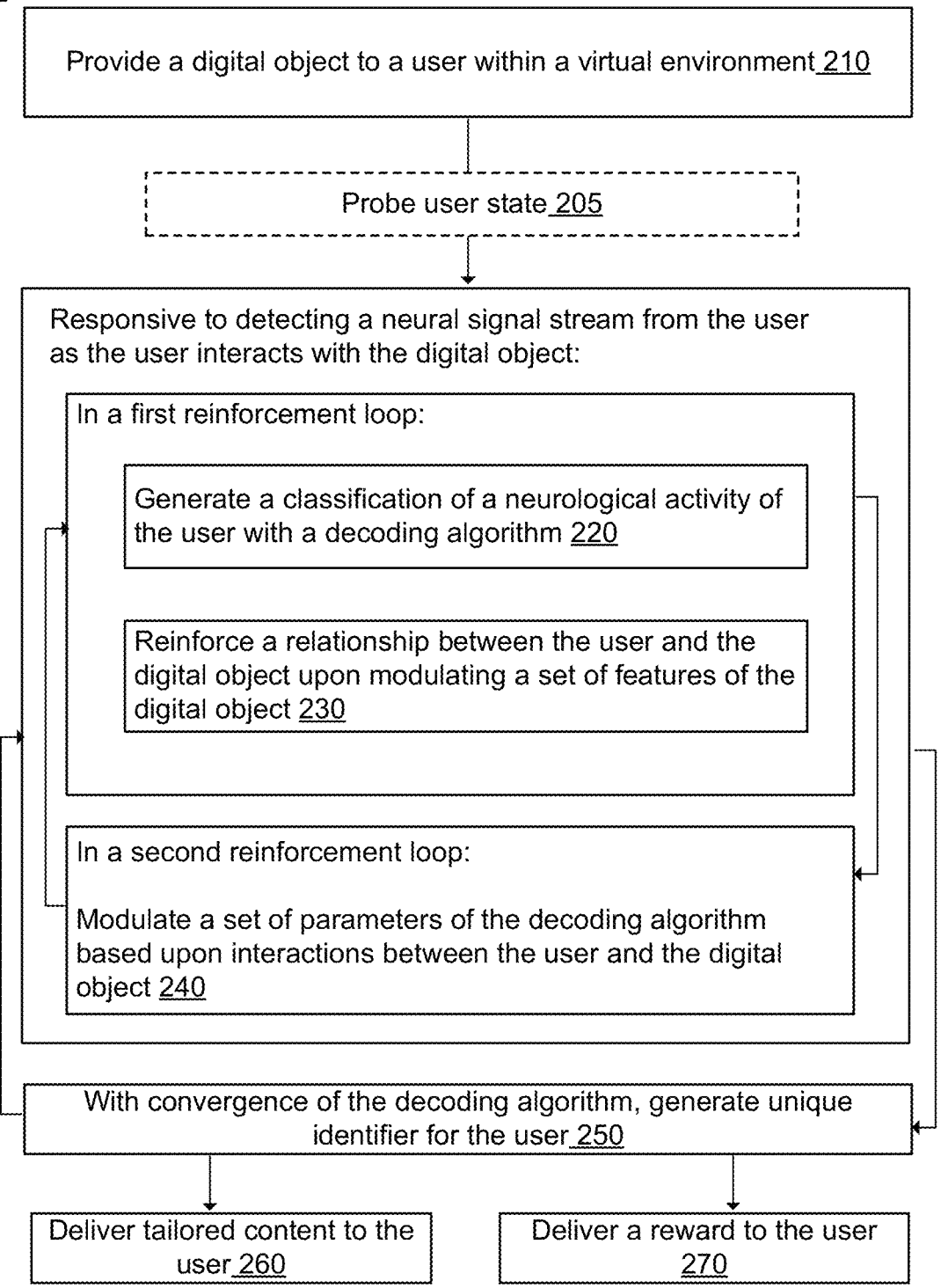
FIG. 2 depicts a flowchart of a method for interactive electronic content delivery in coordination with rapid decoding of brain activity, in accordance with one or more embodiments.

2. Method—Interactive Content Delivery in Coordination with Rapid Decoding of Brain Activity FIG. 2 depicts a flowchart of a method 200 for interactive content delivery with rapid decoding of brain activity as the user interacts with content. As shown in FIG. 2, the hardware platform provides 210 a digital object to a user within a virtual environment through a display, such as the display of the HMD 110 shown in FIG. 1 or other display device. Then, responsive to receiving a neural signal stream from the user as the user interacts with the digital object, computing architecture of the hardware platform implements a first reinforcement loop and a second reinforcement loop contemporaneously and in coordination with the first reinforcement loop. In the first reinforcement loop, as shown in FIG. 2, the computing architecture generates 220 a classification of a neurological activity of the user with a decoding algorithm and reinforces 230 a relationship between the user and the digital object upon modulating a set of features of the digital object. In generating classifications of neurological activity, the computing architecture can extract activity characteristics from sensors of the system (e.g., in relation to spectral content, in relation to neural oscillations, in relation to evoked potentials, in relation to event-related potentials, in relation to different frequency bands of activity, in relation to combinations of activity, etc.), from different electrode channels associated with different brain regions of the user, in order to determine activity states in different regions associated with different brain states. In embodiments, the different brain states analyzed can include one or more of: an alertness state (e.g., a sleep state, alertness level), a state of focus (e.g., focused, distracted, etc.), an emotional state (e.g., happy, angry, sad, bored, scared, calm, confused, surprised, etc.), a mental health state (e.g., a state of anxiety, a state of depression, a state characterized in a manual of mental health conditions, etc.), a neurological health state (e.g. seizure, migraine, stroke, dementia, etc.), a state of sobriety, a state of overt/covert attention, a state of reaction to sensory stimuli, a state of spatial orientation, a state of cognitive load (e.g. of being overloaded), a state of imagery (e.g. of motor action, of visual scenes, of sounds, of procedures, etc.), a memory function state (e.g. encoding effectively, forgetting, etc) and/or any other suitable brain activity state. Such signals can be processed with an adaptive thresholding approach, as described in Section 2.2 below.

In the second reinforcement loop, as shown in FIG. 2, the computing architecture modulates 240 a set of parameters of the decoding algorithm based upon interactions between the user and the digital object, where features of the digital object are dynamically modulated in real time or near-real time. As such, the first and the second reinforcement loops form a mutual learning architecture where features of the digital object are refined to reinforce a relationship with the user (e.g., in terms of level of engagement by the user, in terms of cognitive "comfort" or a reduction in cognitive stress associated with interacting with the digital object, etc.), in coordination with refinement of a decoding algorithm for decoding neurological activities of the user.

As shown in FIG. 2, with convergence of the decoding algorithm, the hardware platform can generate 250 a unique identifier for the user based upon the refined features of the digital object, such that specific feature aspects (or ranges of feature aspects) of a feature space for the digital object can be used for identification of the user. The hardware platform can deliver 260 tailored content to the user and/or deliver 270 a reward to the user based on user cognitive state, a threshold level of convergence of the decoding algorithm, and/or another triggering event, such that the user is provided a tailored experience within a digital universe.

As shown in FIG. 2, the hardware platform can additionally probe a user state 205 using the digital object, another stimulus (e.g., stimuli that are not visible to the user, stimuli that are not consciously perceptible to the user, etc.), and/or another aspect of the virtual environment, and then implement aspects of the method 200 based upon an analysis of the user's cognitive state. For instance, stimuli can include coupling to accelerometer measurements (e.g., peak accelerometer measurements), such that the accelerometer measurements serve as time-locking stimuli. Further detail on probing the user's state is described below in relation to FIGS. 8A and 8B.

The method 200 functions to reinforce relationships between users and digital objects/environments, and implements hardware and computing architecture for improving decoding of neurological activity of users in relation to content provided in a virtual environment, where the content has dynamically modifiable features, and include functionality for authenticating and providing tailored content to users. Such tailored aspects of the virtual environment and objects can also be used to attain a state of comfort or "homeostasis" between a user and a virtual environment that the user is interacting with, and/or to attain other states that the user seeks to attain (e.g. states of memory function, states of attention, empathic states etc.). As described, embodiments of the method 200 can be implemented using one or more embodiments of the system described in Section 1 above; however, embodiments of the method 200 can additionally or alternatively be implemented using other system components.

2.1. Method—Digital Object Provision

Figure 3A:
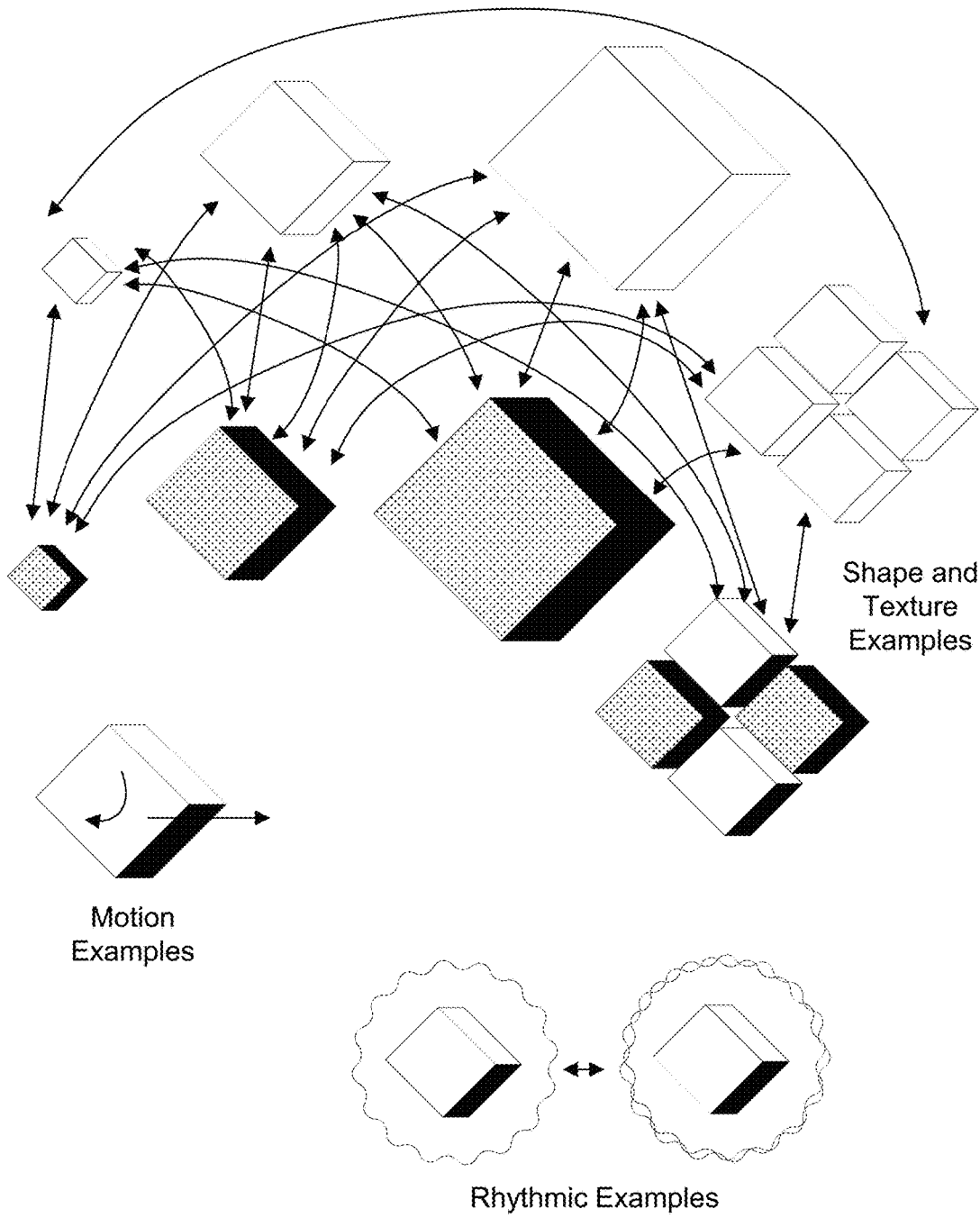
FIG. 3A depicts embodiments of interactive digital objects and modulatable features in accordance with one or more embodiments of the system(s) and method(s) described.

FIG. 3A depicts embodiments of interactive digital objects and modulatable features in accordance with one or more embodiments of the system(s) and method(s) described. In relation to providing 210 a digital object as described in relation to FIG. 2, the digital object includes a set of modulation features that are modulated by the architecture of the first reinforcement loop described in further detail below. In delivering the digital object(s) to the user, the computing architecture of the hardware platform generates instructions for the appearance and behavior of the digital object(s), and transmits the instructions to the HMD or other display device for rendering of the digital object(s) to the user.

The digital object has a body, where the body can define a unit continuum and/or can define multiple unit continuums (e.g., as a set of related objects). In some embodiments where the body is defined as multiple unit continuums, the computing architecture of the hardware platform can generate control instructions that govern motions of the multiple unit continuums about one or more reference features (e.g., a centroid of motion, a path of motion, a volume within which motion is contained, etc.), such that the multiple units behave in a coordinated manner. Additionally or alternatively, in some embodiments where the body is defined as multiple unit continuums, the computing architecture of the hardware platform can generate control instructions that govern motions of one or more of the multiple unit continuums independently.

The set of modulation features includes at least one modifiable morphological feature for tuning a morphology of the body. The morphological feature(s) define one or more of: a geometry of a portion of all of the body, a size of the body, a volumetric feature of the body, and any other morphological aspect of the body. The geometry of the body can include one or more of: prismatic portions (e.g., polygonal prismatic portions), pyramidal portions (e.g., pyramids having base polygonal footprints), portions defined by curvatures (e.g., concave portions, convex portions, etc.), portions defined by surfaces of revolution, amorphous portions, and any other portions defining one or more shape features of the body. The size of the body can be globally adjustable in scale, or can alternatively, subportions of the body can be adjustable in scale (e.g., to skew the body). A volumetric feature of the body can define an internal and/or external volume of the body. FIG. 3A depicts examples of a digital object with a cube-shaped body with modulation features for adjusting size, volume, and multiplicity of the body.

The set of modulation features can also include at least one modifiable motion feature for affecting motion of the body throughout space (e.g., in the virtual environment). As shown in FIG. 3A, the motion feature(s) define one or more of: stillness or static behavior, paths of motion in terms of translation along linear and/or non-linear paths), translation relative to different axes (e.g., in a 3D coordinate system), rotation about different axes (e.g., in a 3D coordinate system), rotation about reference features (e.g., points, lines, volumes, etc.), and/or any other motion features. Motion feature modulation can be implemented by the computing architecture in association with physical constraints or other constraints of the virtual environment, where the constraints define boundaries that the computing architecture uses when modulating motion features of the digital object. For instance, motion of the body of the digital object can be constrained, such that the digital object cannot pass certain boundaries (e.g., walls, other objects) defined by the virtual environment.

The set of modulation features can also include at least one modifiable color feature for affecting a color appearance of the body. The color feature(s) can control color of the entire body and/or subportions of the body, such that individual subportions of the body of the digital object can be controllable in color. The color feature(s) can be selected from one or more color spaces including RGB color space, CMY color space, HSV color space, HIS color space, or another color space. Color features of the digital object and/or associated objects of the virtual environment can produce modulated intensity, saturation, contrast, brightness, hue, and/or other appearances of the digital object.

The set of modulation features can also include at least one modifiable texture feature for affecting a surface texture of the body. The texture feature(s) can control texture of the entire body and/or subportions of the body, such that individual subportions of the body of the digital object can be controllable in texture. Texture features can be defined in terms of perceived or actual smoothness (e.g., in relation to rendering capabilities of the HMD and/or computing architecture), perceived or actual roughness (e.g., in relation to rendering capabilities of the HMD and/or computing architecture), perceived or actual hardness (e.g., in relation to rendering capabilities of the HMD and/or computing architecture), perceived or actual porosity (e.g., in relation to rendering capabilities of the HMD and/or computing architecture), perceived or actual sharpness (e.g., in relation to rendering capabilities of the HMD and/or computing architecture), perceived or actual viscosity (e.g., in relation to rendering capabilities of the HMD and/or computing architecture), perceived or actual friction (e.g., in relation to rendering capabilities of the HMD and/or computing architecture) and/or any other perceived or actual textures.

The set of modulation features can also include at least one modifiable rhythmic feature for affecting a rhythmic behavior of the body (e.g., in relation to audio or haptic features associated with the digital object, as described in further detail below). Rhythmic features can be related to motion features and can additionally or alternatively define one or more of: pulsing behaviors of the digital object(s), rippling behaviors of the digital object(s), translation of the digital object(s) along vectors of motion, rotation of the digital objects, interactions between the digital object(s) and other objects and/or the virtual environment, and other rhythmic features. In an example shown in FIG. 3A the computing architecture can modulate a rhythmic feature of a cube-shaped digital object with a pulsing and rippling wave or bubble defined about the digital object.

Figure 3B:
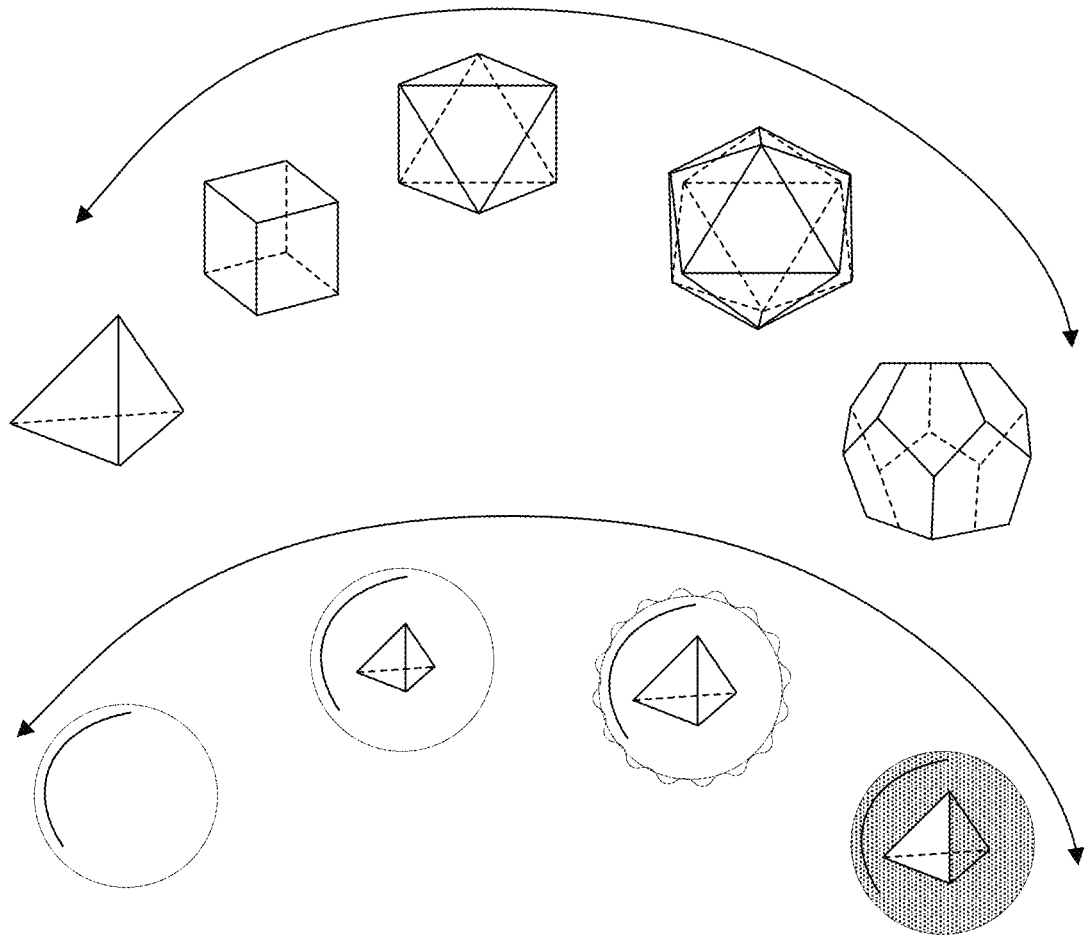
FIG. 3B depicts additional embodiments of interactive digital objects and modulatable features in accordance with one or more embodiments of the system(s) and method(s) described.

FIG. 3B depicts additional embodiments of interactive digital objects and modulatable features in accordance with one or more embodiments of the system(s) and method(s) described. In relation to FIG. 3B, the computing architecture can produce complex feature modulation effects in morphology, color, texture, motion, and other features, with transformations in multiple aspects of a feature space, in relation to implementation of the first and second reinforcement loops described in more detail below. In examples shown in FIG. 3B, the computing architecture can, for instance, transform a morphology of the body of the digital object through different phases having different numbers of sides (e.g., tetrahedral, quadrahedral, quintahedral, etc.). In another example shown in FIG. 3B, the computing architecture can, for instance, transform interior components (e.g., in morphology, color, texture, etc.) and textures/colors of interior and exterior portions of the digital object with complex transformations in modulatable features.

In providing the digital object and modulated forms of the digital object in subsequent portions of the method 200, the computing architecture can include structures for generating other outputs associated with output capabilities of virtual reality devices associated with the HMD and/or BCI. Such outputs can include one or more of audio outputs and haptic outputs, which the computing architecture of the hardware platform can coordinate with digital object provision and/or modulation of features of digital objects.

While modulation of the digital object(s) is described, the hardware platform can also provide and/or modulate aspects of the virtual environment (e.g., in terms of augmented reality content, in terms of virtual reality content, etc.) according to embodiments of portions of the methods described.

As shown in FIGS. 3A and 3B, the computing architecture of the hardware platform can provide digital objects and modulate different modulatable features of the digital objects according to different time scales. In relation to reinforcement architecture of mutual learning algorithms described below, modulation according to different time scales can produce unique responses from users (e.g., in relation to interaction reinforcement, in relation to user authentication, etc.), where the temporal aspects of responses, as captured in neural signals by the BCI, can be used for reinforcement and further modifications to the digital object(s).

As such, in providing the digital object(s) to the user and/or modulating features of the digital object(s) and/or virtual environment based on feedback from the neural decoding algorithm, the computing architecture can modulate temporal behavior of a first modulation feature of the set of modulation features according to a first time scale, and modulate temporal behavior of a second modulation feature of the set of modulation features according to a second time scale different than the first time scale.

The time scales for feature modulation can be on the order of sub-milliseconds, milliseconds, sub-seconds, seconds, minutes, hours, days, and/or of any other suitable time scale. Other time aspects of feature modulation can include phases of feature modulation (e.g., in relation to alternation of modulation of different features). For instance, the computing architecture can alternate between modulation of size and modulation of motion. Other time aspects of feature modulation can include frequency of feature modulation. For instance, a shape of the object can be adjusted multiple times with a set frequency. Other time aspects of feature modulation can include counts of feature modulation. Other time aspects of feature modulation can include pauses between instances of feature modulation, and/or other temporal aspects.

Different features can be modulated according to different time scales. For instance, a shape of the object can be expanded in a first time scale and texture of the object can be altered in a second time scale. The same feature can also be modulated according to different time scales. For instance, a shape of the object can be transformed in a first time scale, and also transformed (e.g., at another time point) according to a second time scale. The same type of features (e.g., morphological features, motion features, etc.) and/or different types of features can also be modulated according to different time scales. The computing architecture can be configured to modulate one or more features according to different time scales, in order to maintain a state of comfort or "homeostasis" between a user and a virtual environment that the user is interacting with.

2.2. Method—Adaptive Thresholding related to Decoding of Brain Activity

Figure 4:
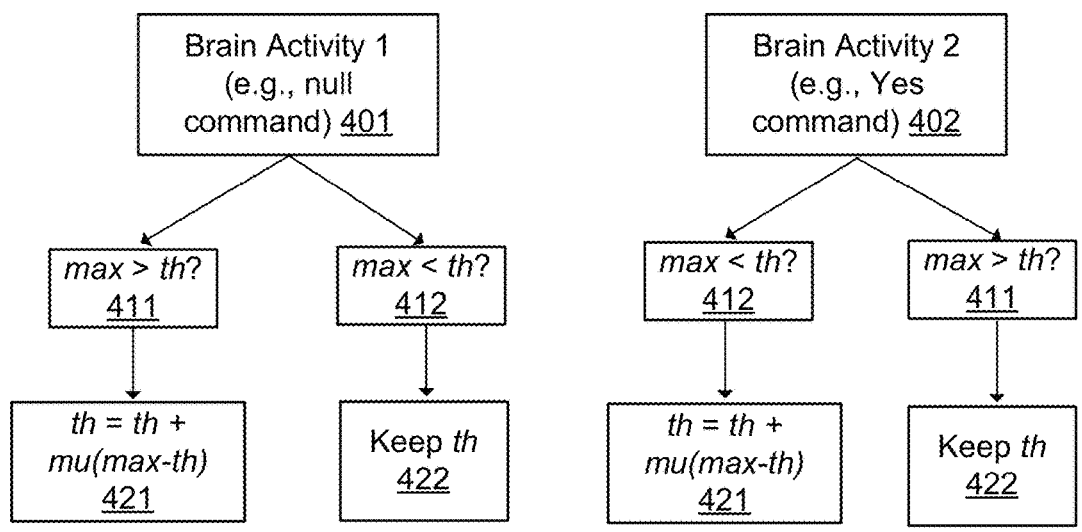
FIG. 4 depicts an embodiment of adaptive thresholding associated with rapid decoding of brain activity, in accordance with one or more embodiments.

FIG. 4 depicts an embodiment of adaptive thresholding associated with rapid decoding of brain activity, in accordance with one or more embodiments. As shown in FIG. 4, the decoding algorithm can include associated architecture 400 for an adaptive threshold operation, where the adaptive threshold operation is applied to incoming neural signal streams generated as the user interacts with the digital object(s) provided in upstream portions of the method 200 described above. The hardware platform applies the adaptive thresholding operation to each of a set of brain activities, where the set of brain activities are associated with interactions with the digital object.

In one embodiment, as shown in FIG. 4 (left), a set of threshold conditions 411, 412 associated with performance of decoding of a first brain activity 401 is applied a neural signal stream capturing a first brain activity 401, where, in FIG. 4, max captures a maximum error in the performance, and th represents the threshold condition. If a maximum error is greater than a threshold and does not satisfy the threshold condition, the computing architecture penalizes 421 the threshold condition with a penalty factor mu. However, if the maximum error is less than (or equal to) a threshold and thus satisfies the threshold condition, the computing architecture retains 422 the threshold condition and does not adjust the penalty factor mu.

As shown in FIG. 4 (right), a set of threshold conditions 411, 412 associated with performance of decoding of a second brain activity 402 is applied a neural signal stream capturing a second brain activity 402, where, in FIG. 4, max captures a maximum error (e.g., in terms of false positives, in terms of false negatives) in the performance, and th represents the threshold condition. If a maximum error is less than a threshold and does not satisfy the threshold condition, the computing architecture penalizes 421 the threshold condition with a penalty factor mu. However, if the maximum error is greater than (or equal to) a threshold and thus satisfies the threshold condition, the computing architecture retains 422 the threshold condition and does not adjust the penalty factor mu. As such, the adaptive thresholding operation includes an adjustable penalty parameter configured to adjust a false classification frequency associated with the decoding (e.g., classification) of the neurological activities of the user. Furthermore, in relation to the maximum error, the changes in the threshold condition with each iteration of the adaptive threshold approach are tied to the magnitude of the error. For instance, a small error leads to gradual progression of the threshold condition, and larger errors lead to larger changes in the threshold condition.

In an example application of the activities shown in FIG. 4, the digital object provided by the hardware platform, in coordination with the HMD, is a deck of cards in a virtual environment. The computing architecture modulates a color of each card that reaches the top of the deck, to produce a green top card or a red top card. The goal of the user, is to indicate selection of the green cards as they reach the top of the deck (e.g., a yes command), and to not indicate election of the red cards as they reach the top of the deck (e.g., a no command). The indicated selection is detected by the BCI, which generates a neural signal stream that is transmitted to and decoded by the hardware platform. As such, in relation to FIG. 4, the first brain activity is a "null" command (indicating non-selection of a card), and the second brain activity is a "yes" command (indicating selection of a card), and the adaptive threshold approach modulates the threshold condition until decoding of "null" and "yes" commands from the neural signal stream satisfies a desired condition.

In relation to FIG. 4, the first brain activity and the second brain activity 402 can be complementary to each other (e.g., in relation to a "yes" command and a "null" command; however, in alternative embodiments of the method, the brain activities may not be complementary to each other and the adaptive thresholding approach can have different architecture.

Figure 5:
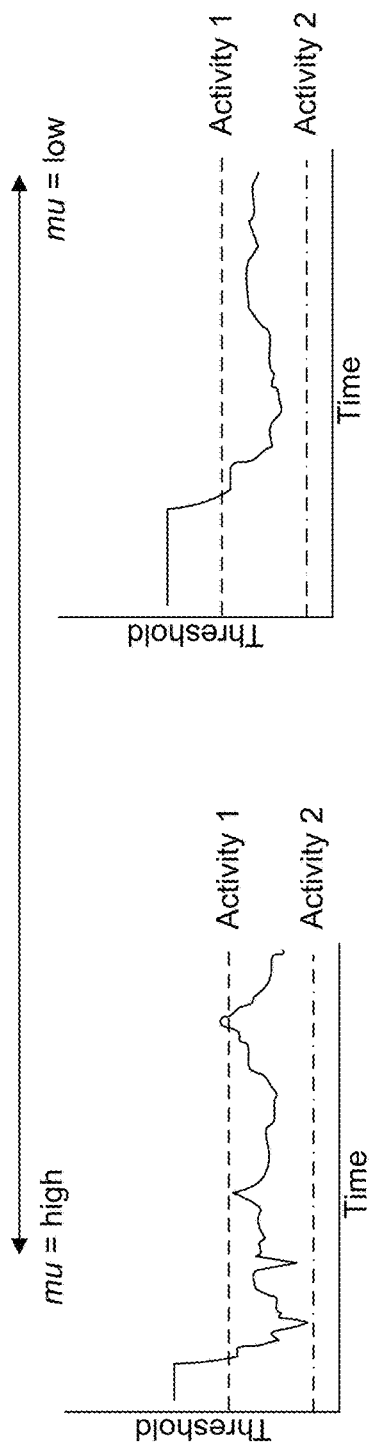
FIG. 5 depicts embodiments of outputs of an adaptive thresholding process using adjustable parameters, in accordance with one or more embodiments.
Figure 5:
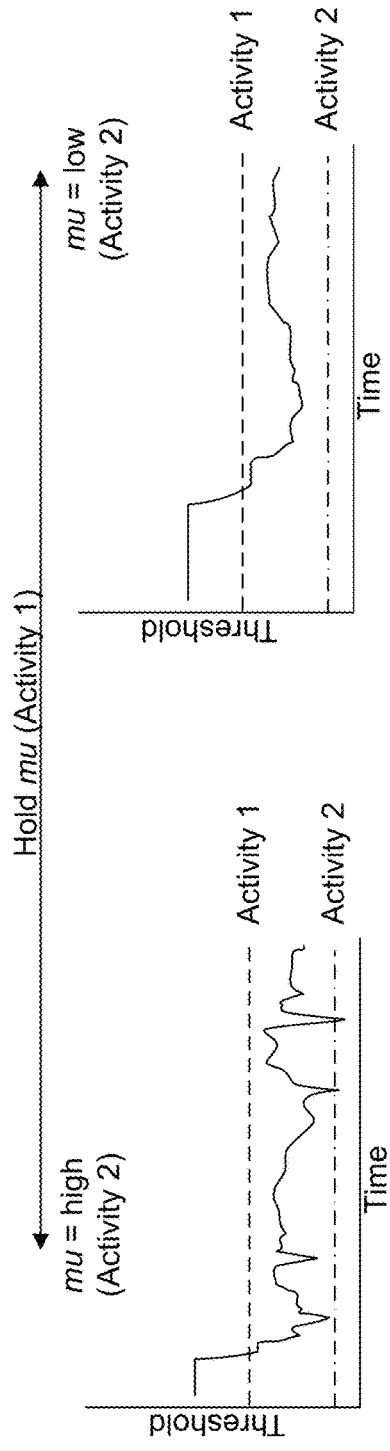

FIG. 5 depicts embodiments of outputs of an adaptive thresholding process using adjustable penalty parameters, in accordance with one or more embodiments. As shown in FIG. 5, and in relation to an embodiment of the approach described in relation to FIG. 4, the computing architecture automatically adjusts threshold conditions based on errors (e.g., false positives, false negatives) and the magnitudes of the errors, with application of a penalty factor, mu. Across or between iterations of the adaptive thresholding approach, decreasing the magnitude of the penalty factor, mu, increases a time to convergence but also increases the accuracy of decoding of a behavior. Conversely, across or between iterations of the adaptive thresholding approach, increasing the magnitude of the penalty factor, mu, decreases a time to convergence but also decreases the accuracy of decoding of a behavior. As such, in relation to decoding of different brain activities, the reinforcement architecture (e.g., the second reinforcement loop described above) can be configured to modulate a learning rate and an accuracy in generating the classification with adjustment of the adjustable penalty parameter.

Furthermore, the computing architecture can adjust the penalty factor, mu, asymmetrically in relation to decoding of different behaviors captured in brain activity of the user. For instance, as shown in FIG. 5, the accuracy of decoding of a first brain activity of the user (e.g., activity 1) satisfies a desired condition, but the accuracy of decoding of a second brain activity of the user (e.g., activity 2) is unsatisfactory. As such, the computing architecture can be configured to hold the value of mu in relation to the adaptive threshold approach for decoding the first brain activity, but decrease the value of mu in relation to the adaptive threshold approach for decoding the second brain activity until performance of the decoding model is satisfactory. Satisfactory decoding can be based on false positive and/or false negative rates in relation to decoding different behaviors captured in neural signal data. In more detail, responses of the user can differ to outputs or modulations of the digital object based on false positives in decoding of behavior and false negatives in decoding of behavior. As such, in relation to decoding of different brain activities, the reinforcement architecture (e.g., the second reinforcement loop described above) can be configured to modulate the adjustable penalty parameter with a first magnitude to reduce a false positive rate in the classification, and with a second magnitude to reduce a false negative rate in the classification.

In the embodiments described in FIGS. 4 and 5, the threshold thus stabilizes with convergence of the decoding algorithm, such that brain activities are accurately decoded with a desired (low) error rate. In relation to other metrics, the computing architecture can characterize convergence of the decoding algorithms based on values of standard deviation-associated parameters for instances of decoded behaviors and/or values of confidences in instances of decoded behaviors, where convergence is characterized by increasing confidence values and decreasing standard deviation associated values for decoded behaviors captured in the neural signal streams detected as the user interacts with virtual content.

Figure 6:
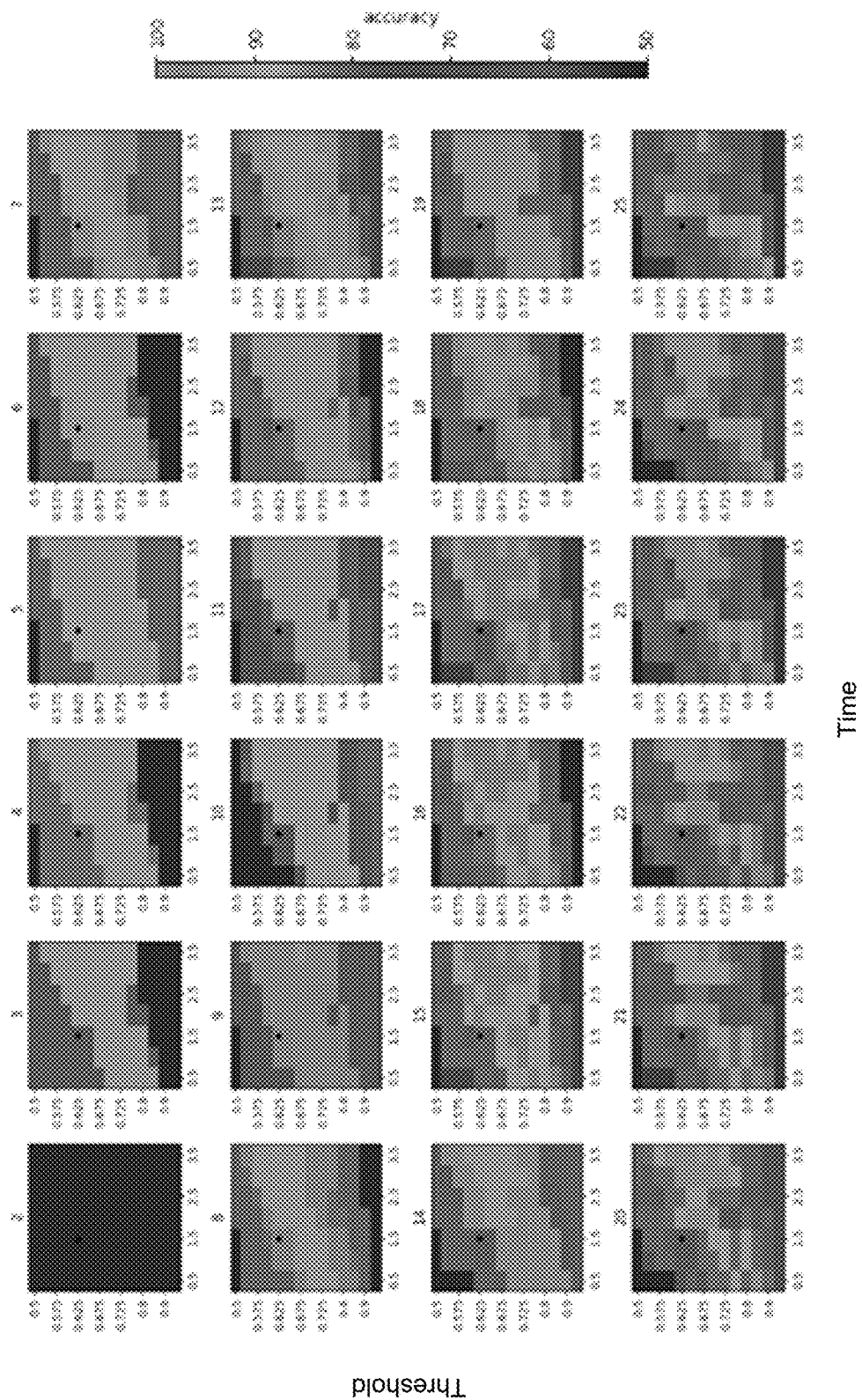
FIG. 6 depicts embodiments of system outputs showing convergence of brain activity decoding associated with a set of events.

FIG. 6 depicts embodiments of system outputs showing convergence of brain activity decoding associated with a set of events. As shown in FIG. 6, over a set of trials, the decoding algorithm of the computing architecture converges such that accuracy at the event level in relation to events associated with different modulatable features of the digital object increases and stabilizes. In FIG. 6, for each of the set of trials, the y-axis represents threshold values associated with each of a set of events of decoding brain activity responses to changes in different modulatable features of the digital object, and the x-axis represent time. For each of the trials shown in FIG. 6, the black dot represents a threshold level to which other thresholds can be compared, and thresholds higher than the level represented by the black dot indicate more accuracy in decoding brain activity for a specific event. As shown in the indicator bar of FIG. 6 (right), the decoding algorithm adjusts thresholds for decoding brain activity associated with each event until thresholds stabilize and decoding accuracy reaches a satisfactory level.

Figure 7A:
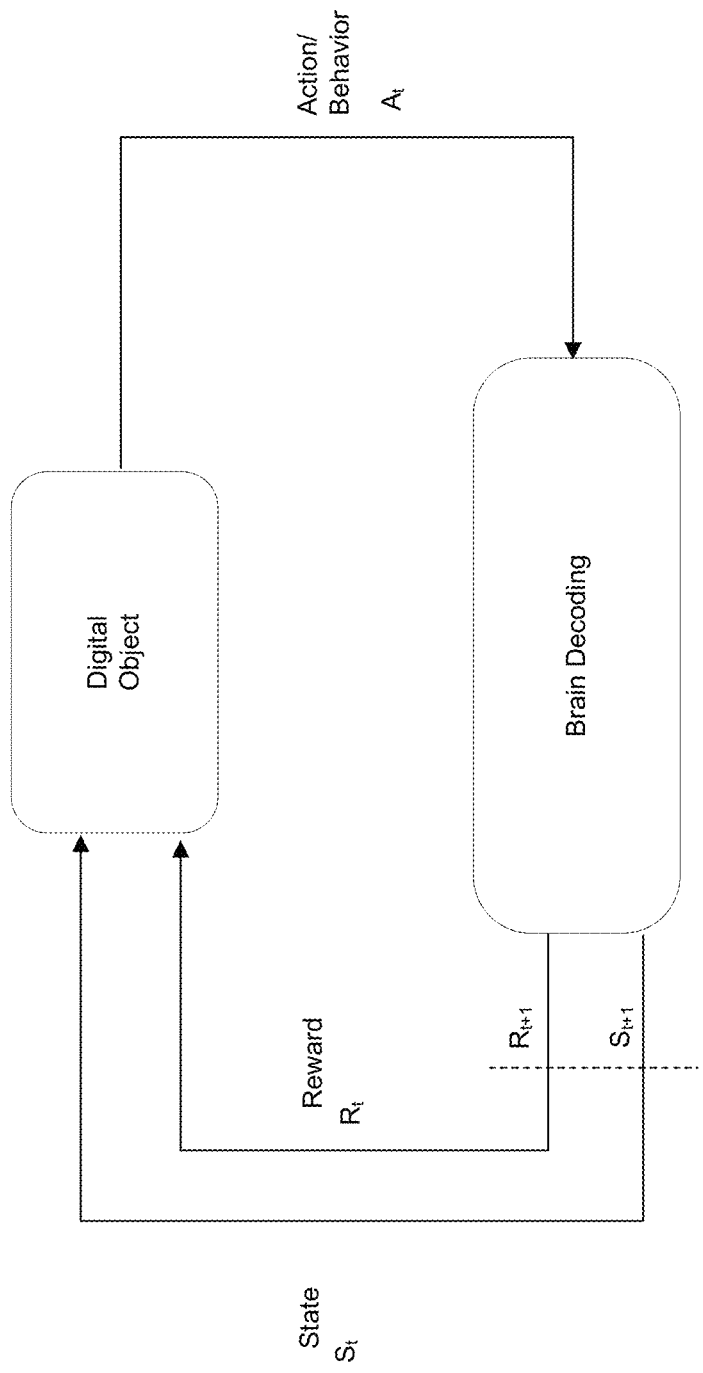
FIG. 7A depicts a schematic of an embodiment of reinforcement architecture for modulation of a digital object and for modulation of a brain decoding algorithm that operate in a coordinated manner in relation to processing neural signals from a user.

FIG. 7A depicts a schematic of an embodiment of reinforcement architecture for modulation of a digital object and for modulation of a brain decoding algorithm that operate in a coordinated manner in relation to processing neural signals from a user. As shown in FIG. 7A, the computing architecture of the hardware platform is constructed with a mutual learning reinforcement framework where, in contemporaneously implemented and coupled reinforcement loops, modulatable features of the provided digital object are adjusted in an iterative manner based on decoded user responses captured in neural signal data, and parameters of the decoding algorithm are also modulated based on responses of the user analyzed from the decoded neural signal data. As shown in FIG. 7A, for each iteration of the digital object (in terms of feature modulation), the user responds consciously or subconsciously, and the action/behavior response $A_t$ is captured in neural signal data generated by the BCI. The neural signal data is transmitted as an input into the decoding algorithm for classification of the neurological activity, where each correctly decoded state output by the decoding algorithm is rewarded (e.g., with a positive score) and each incorrectly decoded state is punished (e.g., with a negative score) in the reinforcement framework. Correctly and incorrectly decoded states are then used by the computing architecture to modulate features of the digital object, in order to reinforce the relationship between the user and the digital object or virtual environment, and the reinforcement framework continues until satisfactory levels of decoding are attained.

Figure 7B:
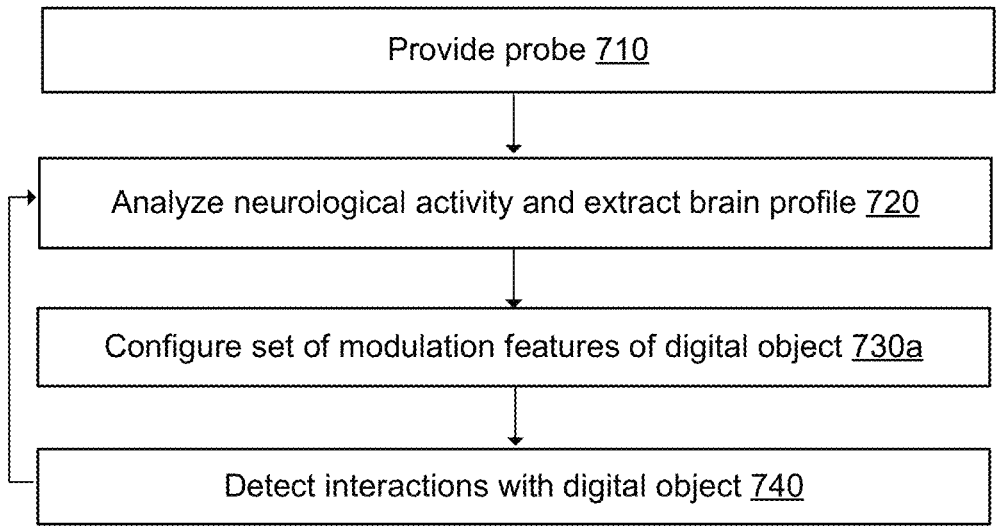
FIG. 7B depicts flowcharts of depicting method flows corresponding to the reinforcement architecture shown in FIG. 7A.
Figure 7B:
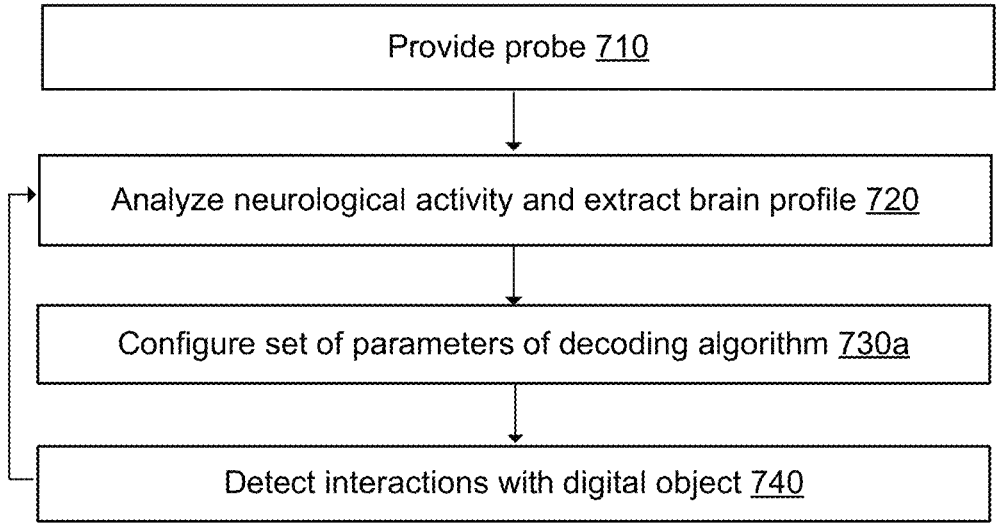

FIG. 7B depicts flowcharts of depicting method flows corresponding to the reinforcement architecture shown in FIG. 7A, with a focus on probing user states with the digital object in order to iterate feature modulation of the digital object and to iterate parameter modulation of the decoding framework.

As shown in FIG. 7B (top), in relation to iteration of modulatable features of the digital object, the computing architecture provides 710 a probe (e.g., a digital object, a feature of the digital object, an aspect of the virtual environment, passive virtual element, etc.), and the computing architecture receives and analyzes 720 neurological activity from the user, through the BCI, in order to extract a brain activity profile of the user as the user interacts with the digital object. Then, the computing architecture configures a set of modulation features of the digital object 730*a* in order to improve likelihood of positive interactions between the user and the virtual environment, and then continues to detect 740 interactions with the modulated digital object. The process shown in steps 720, 730*a*, and 740 repeats until threshold levels of decoding of user cognitive state and/or a sufficiently reinforced relationship between the user and the digital object/virtual environment is reached.

As shown in FIG. 7B (bottom), in relation to iteration of adjusting parameters of the decoding algorithm, the computing architecture provides 710 a probe (e.g., a digital object, a feature of the digital object, an aspect of the virtual environment, passive virtual element, etc.), and the computing architecture receives and analyzes 720 neurological activity from the user, through the BCI, in order to extract a brain activity profile of the user as the user interacts with the digital object. Then, the computing architecture configures a set of adjustable parameters of the decoding algorithm (e.g., such as adaptive thresholding parameters) 730b in order to improve likelihood of positive interactions between the user and the virtual environment, and then continues to detect 740 interactions with the digital object, where detection is implemented using the updated decoding algorithm. The process shown in steps 720, 730b, and 740 repeats until threshold levels of decoding of user cognitive state and/or a sufficiently reinforced relationship between the user and the digital object/virtual environment is reached.

Figure 8A:
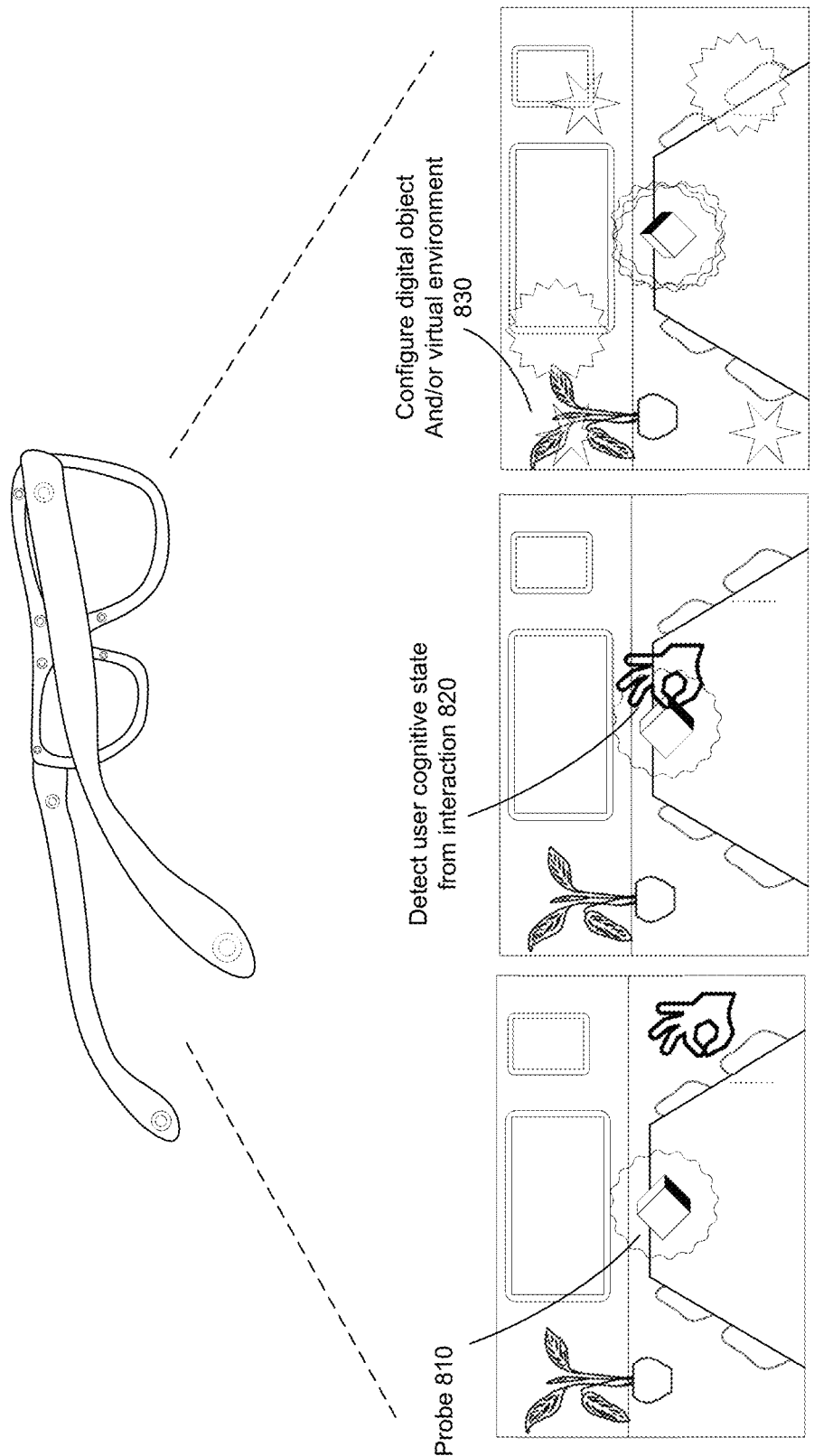
FIG. 8A depicts an embodiment of an environment for probing a user cognitive state and modulating aspects of a digital object and/or environment in accordance with one or more embodiments of the system(s) and method(s) described.

FIG. 8A depicts an embodiment of an environment for probing a user cognitive state and modulating aspects of a digital object and/or environment in accordance with one or more embodiments of the system(s) and method(s) described.

As shown in FIG. 8A, the computing architecture provides a probe 810 through the HMD, and receives neural signals from the BCI as the user consciously or subconsciously responds to the probe 810. The computing architecture uses the neural signals to detect 820 a user cognitive state from the interaction or response to the probe 810. Then, the computing architecture configures aspects of the virtual environment (e.g., a digital object, the probe, scenery of the virtual environment, another portion of the virtual environment) based on the user cognitive state, in order to benefit the user. In one embodiment, benefitting the user can include reducing or otherwise maintaining a low cognitive stress state of the user, such that, in relation to reinforcing relationships between the user and a digital object (or another aspect of the virtual environment), the computing architecture generates a characterization of cognitive stress of the user while the user interacts with the probe, and modulates the features of the digital object based upon the characterization of cognitive stress.

Additionally or alternatively, in embodiments, the computing architecture can provide the probe to determine one or more of: an alertness state (e.g., a sleep state, alertness level), a state of focus (e.g., focused, distracted, etc.), an emotional state (e.g., happy, angry, sad, scared, calm, surprised, etc.), a mental health state (e.g., a state of depression, a state of psychosis, a state characterized in a manual of mental health conditions, etc.), a neurological health state (e.g. seizure, migraine, stroke, dementia, etc.), a state of sobriety, a state of overt/covert attention, a state of reaction to sensory stimuli, a state of cognitive load, a state of imagery (e.g. of motor action, of visual scenes, of sounds, of procedures, etc.), a memory function state, and/or any other suitable brain activity state of the user. The brain activity state(s) can then be used by the computing architecture as inputs to configure an aspect of the virtual environment, through the HMD, and/or to benefit the user in relation to achieving a positive cognitive state. As such, the probe can be used by the computing architecture to generate a cognitive state model (e.g., emotional model) of the user.

As described in more detail below in relation to FIGS. 8B and 9, providing the probe and analyzing cognitive states of the user can be used by the computing architecture for user authentication, where use of the probe can be used by the computing architecture to generate a higher level identifier or profile of the user. Furthermore, understanding user identity can be used by the computing architecture to configure cascades of algorithms associated with decoding brain activity and/or providing tailored content to the user.

In more detail in relation to providing the probe 810, the computing architecture can include structures for entering a user state probing mode in a first time window, wherein in the user state probing mode, the method further comprises generating control instructions for adjusting a set of stimuli provided by the probe, another digital object, and/or the virtual environment. Then, the computing architecture can receive a neural signal stream from the BCI, where receipt of the neural signal stream can be induced in coordination with provision of the probe and be an enriched neural signal stream. The first time window can be associated with initiating a session of interaction with the virtual environment, where, in an example, when the user wants to enter the virtual environment and wears the HMD, the computing architecture enters the user state probing mode (e.g., in response to the user initiating the VR session). Then, in the user state probing mode, the computing architecture extracts, from the BCI, a cognitive state of the user, and contemporaneously (e.g., immediately following, concurrently with, etc.) with the first time window, modulates at least one of the set of modulation features of the digital object and a set of environmental features of the virtual environment based on the cognitive state of the user.

The first time window can, however, be associated with other states of the virtual environment or user states. For instance, the computing architecture can provide the probe periodically throughout a VR session, such that the user is periodically assessed to tune aspects of the virtual environment/digital object based on dynamic cognitive states of the user. Additionally or alternatively, in some embodiments, the computing architecture can provide the probe whenever an aspect of the virtual environment changes significantly, such that the user response to the change is assessed before additional changes are made. Additionally or alternatively, the computing architecture can provide the probe prior to termination of a VR session, such that the user's cognitive state is assessed after a VR session, in relation to content provided during the VR session, to guide delivery of content in subsequent VR sessions.

Aspects of digital objects and/or VR environments that can be used for probing are described further in relation to FIG. 8B below.

Figure 8B:
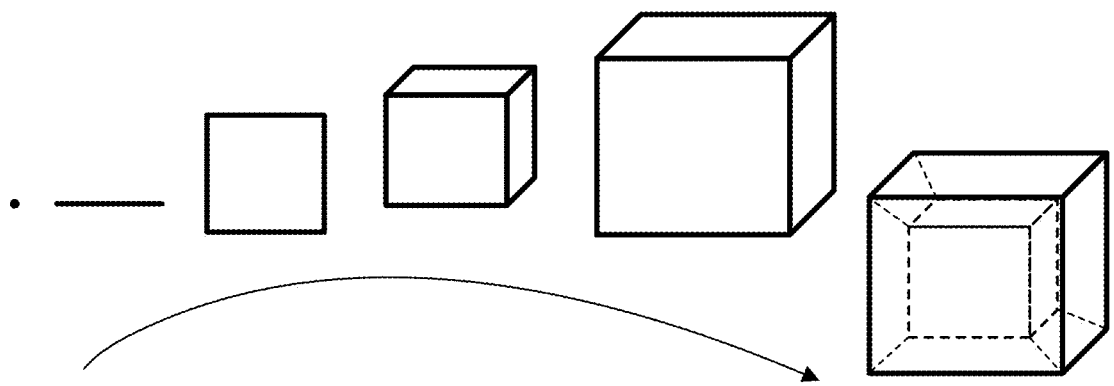
FIG. 8B depicts embodiments of digital objects for probing user state, in accordance with embodiments of the method shown in FIGS. 7A and 7B.
Figure 8B:
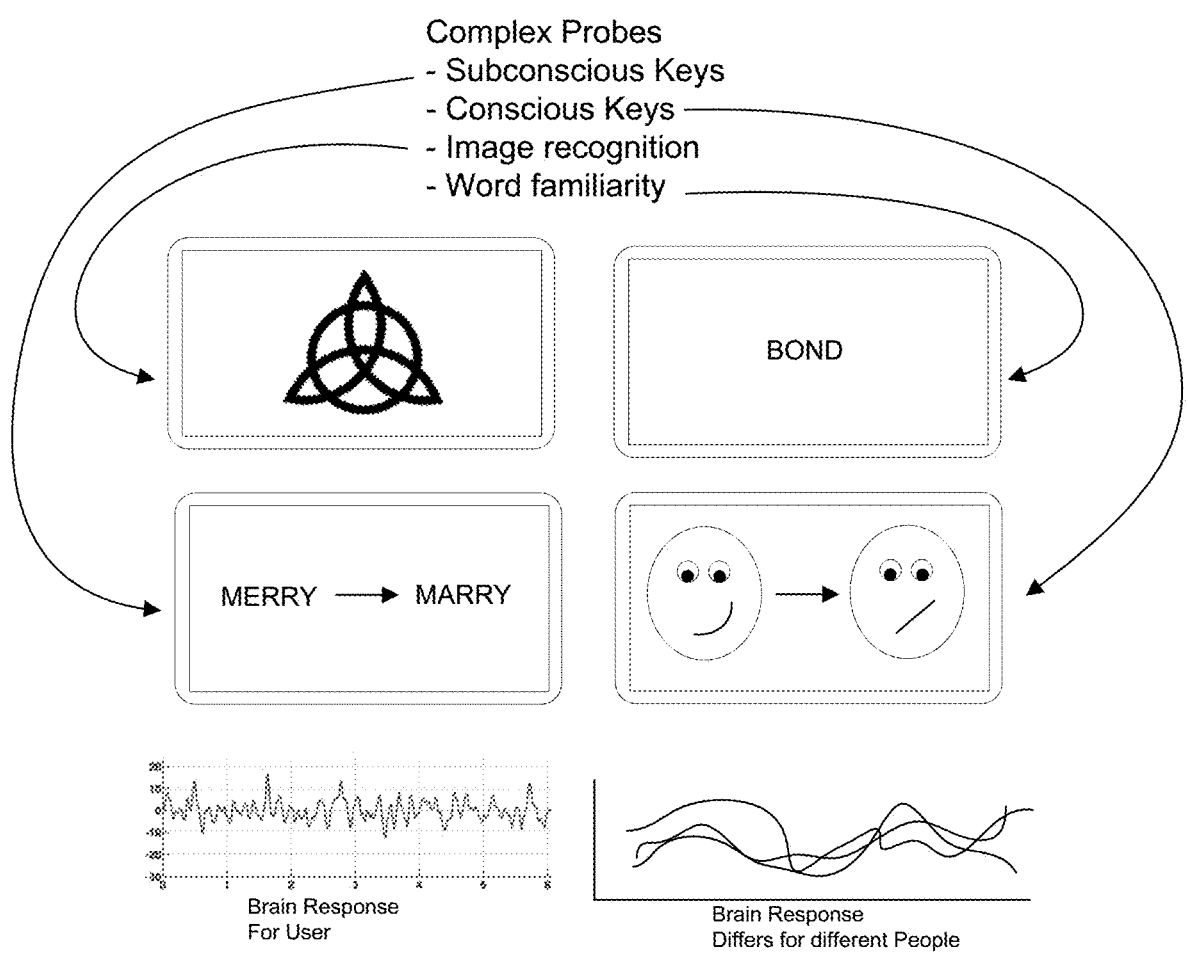

FIG. 8B depicts embodiments of digital objects for probing user state, in accordance with embodiments of the method shown in FIGS. 7A and 7B. As shown in FIG. 8B, the probe can be a digital object that undergoes a transformation, through animations generated by the computing architecture. In examples, the animation can include an emission of light appearing from one or more points or a tesseract expanding slowly from a point (e.g., where transformations occur along one or more time scales). In another example shown in FIG. 8B (top), the animation can include a point object that transforms to a line object that transforms to a plane object that transforms to a cube object that transforms to a tesseract object along a time scale.

Also shown in FIG. 8B (bottom), the probe can be a complex probe of an adapted rapid-serial visual presentation paradigm, where the complex probe includes elements including one or more of: a subconscious key, a conscious key, an image recognition element, and a word familiarity element. In a first example, the complex probe can include an object recognition element, where the object is a complex geometric shape (e.g., including an ellipsoidal object superimposed on a set of radially distributed petal objects). The computing architecture provides the complex probe through the HMD, and modulates features of the complex probe across image frames (e.g., at a rate of 100 ms/image frame), while the BCI collects neural signals from the user and transmits the neural signals to the hardware platform.

Example neural signals from a user, including potentials (e.g., measured as voltages over time) are shown in FIG. 8B (bottom).

In another example, the complex probe can include an audio recognition element, where the audio recognition element includes an audio sample of a known song. The computing architecture provides the complex probe through an audio output device (e.g., an audio output device associated with the HMD), and modulates features of the complex probe (e.g., in terms of tone, pitch, bass, and/or other music parameters), while the BCI collects neural signals from the user and transmits the neural signals to the hardware platform. Features of the complex probe can thus be modulated to deviate from how the audio sample should sound, where the features are provided as stimuli that produce a subconscious or conscious response that is measurable in brain activity of the user.

In another example, the complex probe can include a text element, where the text recognition element includes a image or audio sample of a known word or phrase. The computing architecture provides the complex probe through a display and/or audio output device (e.g., a display or an audio output device associated with the HMD), and the BCI collects neural signals from the user and transmits the neural signals to the hardware platform. In the example shown in FIG. 8B (bottom), the text element depicts the word "BOND", which, for different users, can have different connotations. For instance, users in the financial industry, film industry, chemistry field, legal industry, medical industry, construction industry, psychology field, anthropology field, etc. will each have a different cognitive response to the provided text stimulus, which is detected by the computing architecture upon processing signals from the BCI. As such, the system can authenticate the user by delivering a text object having a set of connotations, in digital format, to the user within the virtual environment, extracting a response of the user to the text object through the BCI, wherein a characteristic of the user corresponds to at least one of the set of connotations, and authenticating the user based on the response.

In another example, the complex probe can include a text element with modulatable features, where the text recognition element includes an image or audio sample of a known word or phrase. The computing architecture provides the complex probe through a display and/or audio output device (e.g., a display or an audio output device associated with the HMD), modulates features of the complex probe, and the BCI collects neural signals from the user and transmits the neural signals to the hardware platform. In the example shown in FIG. 8B (bottom), letters of the word "MERRY" in the text element are modulated (e.g., at a frequency of 100 ms/image frame) to produce other sensible (e.g., "MARRY", "MARY") or nonsensical words, which produce user responses that are detected by the computing architecture upon processing signals from the BCI.

In another example, the complex probe can include an image element with modulatable features, where the image recognition element includes an image of a known entity (e.g., celebrity, public figure). The computing architecture provides the complex probe through a display (e.g., a display associated with the HMD), modulates features of the complex probe, and the BCI collects neural signals from the user and transmits the neural signals to the hardware platform. In the example shown in FIG. 8B (bottom), the expression of the entity in the image is modulated (e.g., at a frequency of 100 ms/image frame) to produce other expressions, which produce user responses that are detected by the computing architecture upon processing signals from the BCI. In a related example, features of the entity in the image can be modulated to be nonsensical (e.g., the image of the entity can be modulated to give the entity a ridiculous headpiece or costume), which produces user responses that are detected by the computing architecture upon processing signals from the BCI.

As described above in relation to digital objects, probe provision can be coordinated with other outputs (e.g., audio outputs, haptic outputs, etc.), such that the probe includes visual and non-visual stimuli.

Furthermore, aspects of the probe and/or responses to the probe, as detected by the hardware platform in communication with the BCI, can be used to determine an identity of the user and/or to generate an authentication of an identity of the user, as described in U.S. application Ser. No. 15/645,169 titled "System and Method for Authentication, Authorization, and Continuous Assessment of User Profiles" and filed on 10 Jul. 2017, which is herein incorporated in its entirety by this reference.

Figure 9:
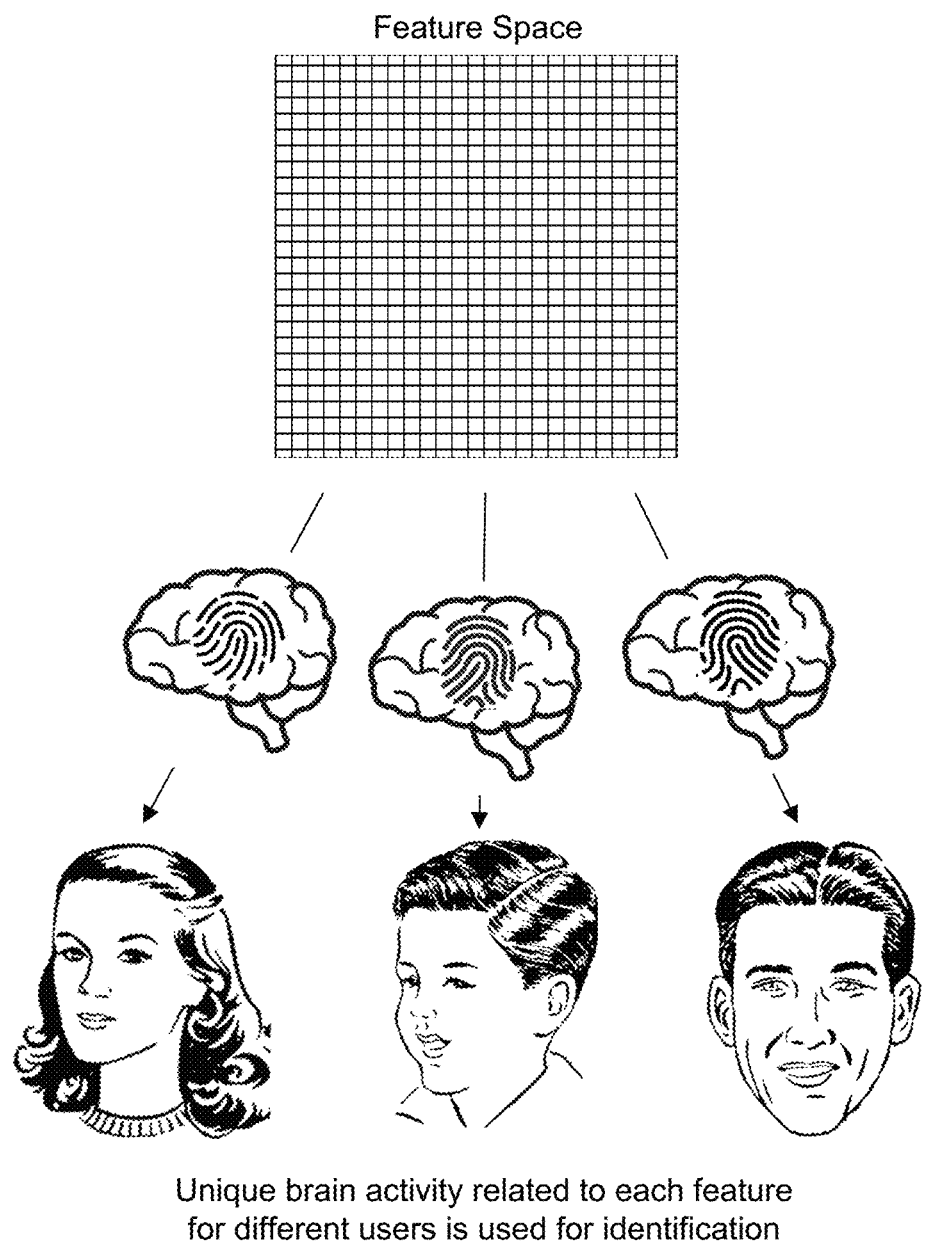
FIG. 9 depicts a schematic representative of user identifiers generated by the system, based user-specific responses to each of a set of features in a feature space.

FIG. 9 depicts a schematic representative of user identifiers generated by the system, based user-specific responses to each of a set of features in a feature space. As the decoding algorithm converges, the computing architecture can output, for each of a set of features in a feature space associated with modulation of a digital object or probe, a signature for the user. The collection of signatures for each of the set of features across the feature space can form a unique signature profile for the user that differentiates the user from other users associated with the method. As such, with convergence of the decoding algorithm, the computing architecture generates a unique identifier for the user, the unique identifier comprising a set of signatures corresponding to cognitive responses of the user to reinforced versions of the set of modulation features for the digital object. As such, in relation to providing probes or other digital objects, digital objects that are reinforced to user preferences can be used by the computing architecture as a basis for generating unique identifiers for each user, where the unique identifiers can serve as neurobiometric identifiers for the users.

In relation to cognitive states (e.g., affective/emotional states, states of stress, states of health conditions, etc.) can, in addition to identifying users, also be used by the computing architecture to identify cognitive states for those specific users. Thus, in an example, the computing architecture can generate multiple unique identifiers for a user, including a first unique identifier that identifies the user in a first (e.g., unstressed) state, and a second unique identifier that identifies the user in a second (e.g., stressed) state, where both the first and the second unique identifiers distinctly identify the user, but also differentiate between different cognitive states of the user.

Furthermore, in subsequent probing and/or reinforcing sessions, the computing architecture can refine the unique identifier over time, to further differentiate the generated unique identifier of the user from unique identifiers for other users. Thus, with iteration of the method, unique identifiers can be further refined. Then, with use of the system by the user, the reinforced digital object and the user's response to the reinforced digital object can be used not only to probe the user's state, but also to authenticate the user and/or to provide tailored content to the user within the virtual environment. In examples the tailored content can include one or more of: music that the user prefers in the cognitive state that the user is in, virtual lessons (e.g., instrument playing lessons) of interest to the user, rewards (e.g., visuals of swimming fish, other pleasing content) deliverable in a virtual environment, or other rewards.

Figure 10:
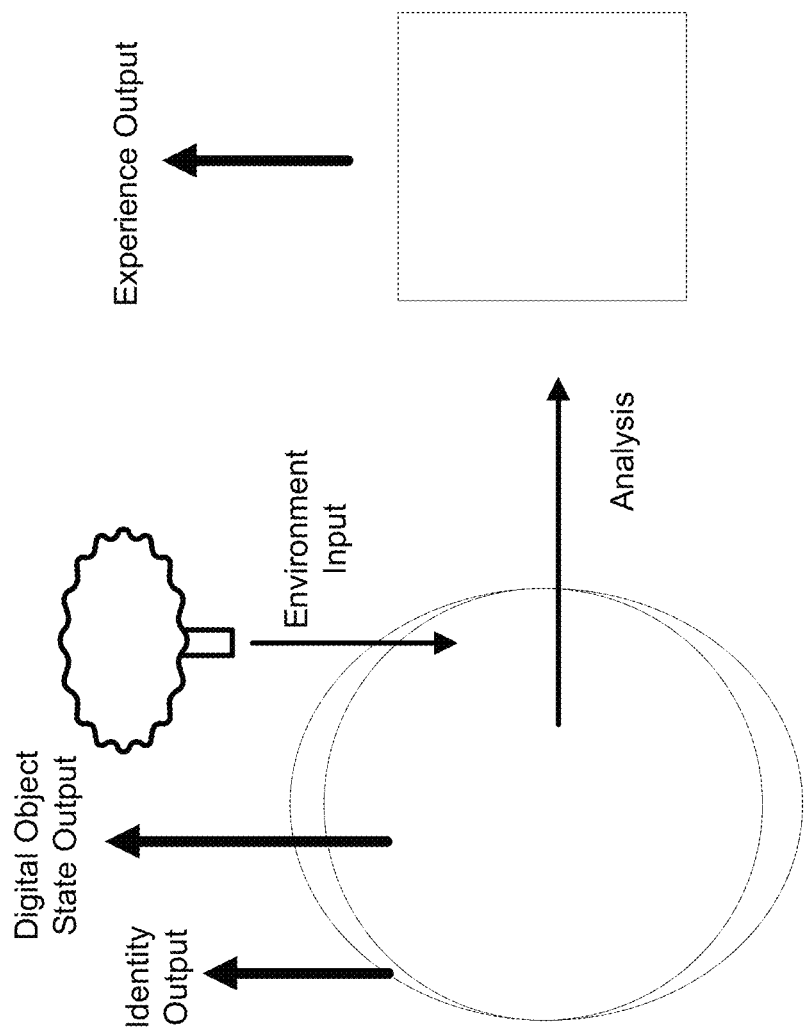
FIG. 10 depicts an embodiment of inputs and application programming interface outputs associated with one or more embodiments of the method(s) and system(s) described.

FIG. 10 depicts an embodiment of inputs and application programming interface (API) outputs associated with one or more embodiments of the method(s) and system(s) described. The system architecture and methods shown in FIG. 10 can be used for continuous authentication and to generate high-level multimodal models that account for contexts external to and internal to the brain of the user, in order to rapidly decode user states and/or to provide relevant outputs to third parties (e.g., third parties associated with content that the user interacts with). In FIG. 10, environment inputs (e.g., a tree observed by the user, an object in the environment of the user) produces a response that is processed by the computing architecture of the system to modulate digital object states, output unique identifiers for users, and/or authenticate a user. The computing architecture can also provide outputs (e.g., upon receiving API requests) as a "multi-faceted snapshot" of user digital object features and user responses to those features, which collectively describe an experience while interacting with the system.

4. Conclusion

The systems and methods described can confer benefits and/or technological improvements, several of which are described below:

The systems and methods can rapidly decode user brain activity states and dynamically generate customized digital objects and/or virtual environments with provision to users in near real time based the decoded brain activity states, with receipt of signals from brain computer interfaces. In particular the system includes architecture for rapidly decoding user states in a manner that can be used to provide digital content to the user in relation to dynamically changing user cognitive states. As such, the systems and methods can improve function of virtual reality, augmented reality, and/or brain computer interface devices relation to improved content delivery through devices that are subject to limitations in functionality.

The systems and methods can additionally efficiently process and deliver large quantities of data (e.g., neural signal data) by using a streamlined processing pipeline. Such operations can improve computational performance for data in a way that has not been previously achieved, and could never be performed efficiently by a human. Such operations can additionally improve function of a system for delivering digital content to a user, where enhancements to performance of the virtual system provide improved functionality and application features to users of the virtual system.

Furthermore, the systems and methods generate novel user identification objects, based on reinforced versions of digital objects tuned to neurological signatures of the user. Such novel objects serve as neurobiometric elements that can be used to differentiate identities of different users in a way that has not been achieved before.

The foregoing description of the embodiments has been presented for the purpose of illustration; it is not intended to be exhaustive or to limit the patent rights to the precise forms disclosed. Persons skilled in the relevant art can appreciate that many modifications and variations are possible in light of the above disclosure.

Some portions of this description describe the embodiments in terms of algorithms and symbolic representations of operations on information. These algorithmic descriptions and representations are commonly used by those skilled in the data processing arts to convey the substance of their work effectively to others skilled in the art. These operations, while described functionally, computationally, or logically, are understood to be implemented by computer programs or equivalent electrical circuits, microcode, or the like. Furthermore, it has also proven convenient at times, to refer to these arrangements of operations as modules, without loss of generality. The described operations and their associated modules may be embodied in software, firmware, hardware, or any combinations thereof.

Any of the steps, operations, or processes described herein may be performed or implemented with one or more hardware or software modules, alone or in combination with other devices. In one embodiment, a software module is implemented with a computer program product comprising a computer-readable medium containing computer program code, which can be executed by a computer processor for performing any or all of the steps, operations, or processes described. The computer can be a specialized computer designed for user with a virtual environment.

Embodiments may also relate to an apparatus for performing the operations herein. This apparatus may be specially constructed for the required purposes, and/or it may comprise a general-purpose computing device selectively activated or reconfigured by a computer program stored in the computer. Such a computer program may be stored in a non-transitory, tangible computer readable storage medium, or any type of media suitable for storing electronic instructions, which may be coupled to a computer system bus. Furthermore, any computing systems referred to in the specification may include a single processor or may be architectures employing multiple processor designs for increased computing capability.

Embodiments may also relate to a product that is produced by a computing process described herein. Such a product may comprise information resulting from a computing process, where the information is stored on a non-transitory, tangible computer readable storage medium and may include any embodiment of a computer program product or other data combination described herein.

Finally, the language used in the specification has been principally selected for readability and instructional purposes, and it may not have been selected to delineate or circumscribe the patent rights. It is therefore intended that the scope of the patent rights be limited not by this detailed description, but rather by any claims that issue on an application based hereon. Accordingly, the disclosure of the embodiments is intended to be illustrative, but not limiting, of the scope of the patent rights, which is set forth in the following claims.

What is claimed is:

1. A method for improving decoding of neurological activities, the method comprising:
   providing a digital object to a user within a virtual environment;
   detecting a neural signal stream from a brain computer interface (BCI) coupled to the user, as the user interacts with the digital object;
   in a first reinforcement loop implemented in a first time window:
   generating a first classification of a neurological activity of the user upon processing the neural signal stream with a decoding algorithm,
   in response to the first classification indicating a stressed state, modulating a first set of a plurality of modulation features of the digital object to induce an unstressed state, and in response to the first classification indicating an unstressed state, modulating a second set of the plurality of modulation features of the digital object to maintain the unstressed state, and in a second reinforcement loop implemented in a second time window subsequent to the first time window:
generating a second classification of neurological activity of the user as the user interacts with the modulated digital object, and
modulating a set of parameters of the decoding algorithm based on a comparison of the first classification to the second classification.

2. The method of claim 1, wherein the digital object comprises a body, and wherein the plurality of modulation features comprises a morphological feature associated with a shape of the body, a motion feature associated with motion of at least a portion of the body, a color feature, a rhythmic feature, a sonic feature, a geospatial feature, an animated feature, and a transformation feature.

3. The method of claim 2, further comprising, in the first reinforcement loop, modulating temporal behavior of a first modulation feature of the plurality of modulation features according to a first time scale, and modulating temporal behavior of a second modulation feature of the plurality of modulation features according to a second time scale different than the first time scale.

4. The method of claim 1, wherein processing the neural signal stream with the decoding algorithm comprises implementing an adaptive thresholding operation comprising an adjustable penalty parameter configured to adjust a false classification frequency associated with the classification of the neurological activity of the user.

5. The method of claim 4, further comprising, in the second reinforcement loop, modulating the adjustable penalty parameter with a first magnitude to reduce a false positive rate in the classification, and with a second magnitude to reduce a false negative rate in the classification.

6. The method of claim 5, further comprising modulating a learning rate and an accuracy in generating the classification with adjustment of the adjustable penalty parameter.

7. The method of claim 1, further comprising reinforcing a relationship between the user and the digital object by generating a characterization of cognitive and affective changes of the user while interacting with the digital object and the virtual environment, and modulating the set of modulation features of the digital object and the virtual environment based upon the characterization of cognitive and affective changes.

8. The method of claim 1, further comprising: entering a user state probing mode in a third time window, wherein in the user state probing mode, the method further comprises generating control instructions for adjusting a set of stimuli of at least one of the digital object and the virtual environment, and receiving an enriched neural signal stream from the BCI.

9. The method of claim 8, further comprising, in the user state probing mode, extracting a cognitive state comprising an affective state of the user and an authentication of an identity of the user, and in the third time window, modulating at least one of the set of modulation features of the digital object and a set of environmental features of the virtual environment based on the cognitive state of the user.

10. The method of claim 1, further comprising: with convergence of the decoding algorithm, generating a unique identifier for the user, the unique identifier comprising a set of unique signatures corresponding to cognitive responses of the user to reinforced versions of the set of modulation features for the digital object.

11. The method of claim 10, further comprising refining the unique identifier and continuously authenticating the user based on the unique identifier during implementation of the first reinforcement loop and the second reinforcement loop.

12. The method of claim 11, wherein continuously authenticating the user comprises delivering a text object having a set of connotations, in digital format, to the user within the virtual environment, extracting a response of the user to the text object through the BCI, wherein a characteristic of the user corresponds to at least one of the set of connotations, and authenticating the user based on the response.

13. The method of claim 1, further comprising: upon convergence of the decoding algorithm, with generation of reinforced versions of the set of modulation features of the digital object for the user: delivering tailored digital content to the user within the virtual environment.

14. The method of claim 1, further comprising delivering digital content, as a reward to the user, within the virtual environment, in response to convergence of the decoding algorithm.

15. A system comprising:
a hardware platform configured to couple to a brain computer interface (BCI) worn at a head region of a user, the hardware platform comprising:
an electronics subsystem for conditioning outputs of the BCI; and
a computing subsystem in communication with the electronics subsystem and comprising a non-transitory computer-readable storage medium containing computer program code for operating in:
a content delivery mode that provides a digital object to a user within a virtual environment;
a detection mode that detects a neural signal stream from the BCI, as the user interacts with the digital object;
a first reinforcement architecture defining a first loop implemented in a first time window, wherein, in the detection mode, the first reinforcement architecture:
generates a first classification of a neurological activity of the user upon processing the neural signal stream with a decoding algorithm,
in response to the first classification indicating a stressed state, modulates a first set of a plurality of modulation features of the digital object, and
in response to the first classification indicating an unstressed state, modulating a second set of the plurality of modulation features of the digital object to maintain the unstressed state; and
a second reinforcement architecture defining a second loop implemented in a second time window subsequent to the first time window, wherein in the detection mode, the second reinforcement architecture:
generates a second classification of neurological activity of the user as the user interacts with the modulated digital object, and
modulates a set of parameters of the decoding algorithm based on a comparison of the first classification to the second classification.

16. The system of claim 15, wherein the hardware platform comprises an input unit for receiving at least one of electrical surface signals, optical signals, and single neuron signals.

17. The system of claim 15, wherein the digital object comprises a body, and wherein the content delivery mode comprises architecture for the set of modulation features comprising a morphological feature associated with a shape of the body, a motion feature associated with motion of at least a portion of the body, a color feature, and a rhythmic feature.

18. The system of claim 15, wherein the detection mode comprises architecture for processing the neural signal stream with the decoding algorithm and implementing an adaptive thresholding operation comprising an adjustable penalty parameter configured to adjust a false classification frequency associated with the classification of the neurological activity of the user by the first reinforcement architecture.

19. The system of claim 15, wherein the first reinforcement architecture comprises architecture for generating a characterization of a cognitive state of the user while interacting with at least of the digital object and the virtual environment, and modulating the set of modulation features of the digital object based upon the characterization of cognitive state.

20. The system of claim 15, further comprising an authentication unit comprising architecture for generating a unique identifier for the user with convergence of the decoding algorithm of the first reinforcement architecture and the second reinforcement architecture, the unique identifier comprising a set of unique signatures corresponding to cognitive responses of the user to reinforced versions of the set of modulation features for the digital object.

* * * * *

UNITED STATES PATENT AND TRADEMARK OFFICE
CERTIFICATE OF CORRECTION

PATENT NO. : 12,147,603 B2
APPLICATION NO. : 18/303382
DATED : November 19, 2024
INVENTOR(S) : Furman et al.

Page 1 of 1

It is certified that error appears in the above-identified patent and that said Letters Patent is hereby corrected as shown below:

In the Claims

In Column 24, in Claim 19, Line 6, after "least" insert -- one --.

Signed and Sealed this
Twenty-third Day of September, 2025

John A. Squires
*Director of the United States Patent and Trademark Office*